United States Patent
Johnson et al.

(10) Patent No.: US 11,351,530 B2
(45) Date of Patent: Jun. 7, 2022

(54) LIGHT-ASSISTED PHOTOCATALYST REGENERATION AND OXYGEN-RESILIENT RADICAL POLYMERIZATION

(71) Applicant: MASSACHUSETTS INSTITUTE OF TECHNOLOGY, Cambridge, MA (US)

(72) Inventors: Hadley Sikes Johnson, Arlington, MA (US); Hector Alan Aguirre Soto, Somerville, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 614 days.

(21) Appl. No.: 15/804,969

(22) Filed: Nov. 6, 2017

(65) Prior Publication Data

US 2018/0126367 A1    May 10, 2018

Related U.S. Application Data

(60) Provisional application No. 62/418,247, filed on Nov. 6, 2016.

(51) Int. Cl.
| | | |
|---|---|---|
| *B01J 35/00* | (2006.01) | |
| *G01N 21/64* | (2006.01) | |
| *B01J 31/04* | (2006.01) | |
| *C07D 311/82* | (2006.01) | |
| *C07C 409/00* | (2006.01) | |
| *C07D 311/80* | (2006.01) | |
| *C08F 2/48* | (2006.01) | |
| *C08F 4/32* | (2006.01) | |
| *C08J 3/075* | (2006.01) | |

(Continued)

(52) U.S. Cl.
CPC ............ *B01J 35/004* (2013.01); *B01J 31/04* (2013.01); *C07C 409/00* (2013.01); *C07D 311/80* (2013.01); *C07D 311/82* (2013.01); *C08F 2/48* (2013.01); *C08F 4/32* (2013.01); *C08J 3/075* (2013.01); *C08L 101/14* (2013.01); *G01N 21/64* (2013.01); *B01J 31/0202* (2013.01); *B01J 2231/125* (2013.01); *B01J 2231/70* (2013.01); *C08F 26/10* (2013.01); *C08F 2400/02* (2013.01); *C08F 2438/01* (2013.01); *C08J 2300/14* (2013.01); *C08L 2203/02* (2013.01); *G01N 2021/6417* (2013.01)

(58) Field of Classification Search
CPC ........ B01J 35/004; B01J 35/002; B01J 35/00; B01J 31/04; B01J 31/02; B01J 31/00
USPC .......................................................... 436/85
See application file for complete search history.

(56) References Cited

U.S. PATENT DOCUMENTS

2014/0112960 A1* 4/2014 Lin ..................... A61K 47/34
424/400

OTHER PUBLICATIONS

Van de Linde, Photoinduced formation of reversible dye radicals and their impact on super-resolution imaging, Photochem. Photobiol. Sci., 2011, 10, 499-506. (Year: 2011).*

(Continued)

*Primary Examiner* — Christine T Mui
(74) *Attorney, Agent, or Firm* — Honigman LLP

(57) ABSTRACT

A photocatalyst can be regenerated with increasing efficiency, turnover number and turnover frequency in the presence of air by irradiating the photocatalyst with a first range of wavelengths of light that excite the photocatalyst to an intermediate and irradiating the intermediate with a second range of wavelengths of light that turns the intermediate to the photocatalyst.

14 Claims, 22 Drawing Sheets

(51) Int. Cl.
    *C08L 101/14*     (2006.01)
    *B01J 31/02*     (2006.01)
    *C08F 26/10*     (2006.01)

(56) References Cited

OTHER PUBLICATIONS

Hari, Synthetic applications of eosin Y in photoredox catalysis, Chem. Commun. 2014, 50, 6688-6699. (Year: 2014).*

Ghosh, I.; Ghosh, T.; Bardagi, J. I.; Koenig, B. Reduction of aryl halides by consecutive visible light-induced electron transfer processes. Science 2014, 346, 725-728. (Year: 2014).*

Ghosh, I.; Ghosh, T.; Bardagi, J. I.; Koenig, B. Supplemental Materials for: Reduction of aryl halides by consecutive visible light-induced electron transfer processes. Science 2014, 346, 725-728. (Year: 2014).*

Aguirre-Soto, Alan et al, Excitation of Metastable Intermediates in Organic Photoredox Catalysis: Z-Scheme Approach Decreases Catalyst Inactivation, ACS Catalysis 2018 8 (7), 6394-6400. (Year: 2018).*

* cited by examiner

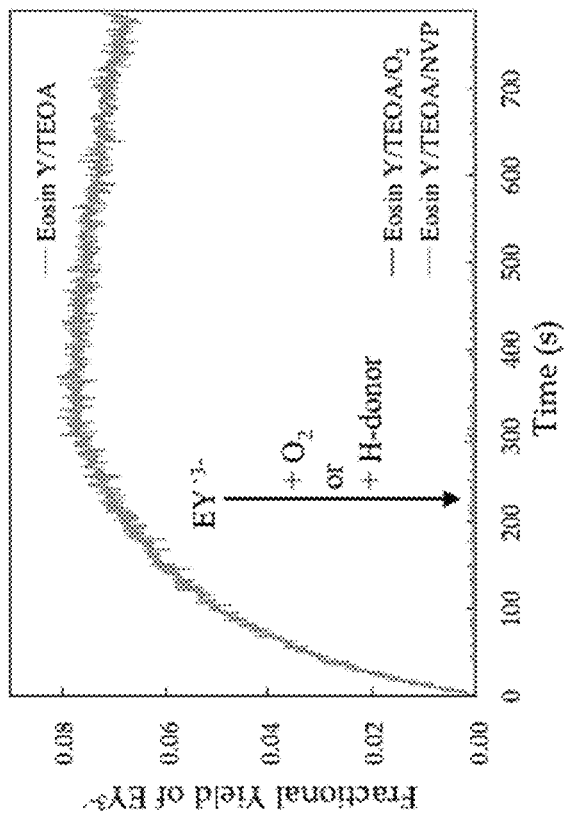
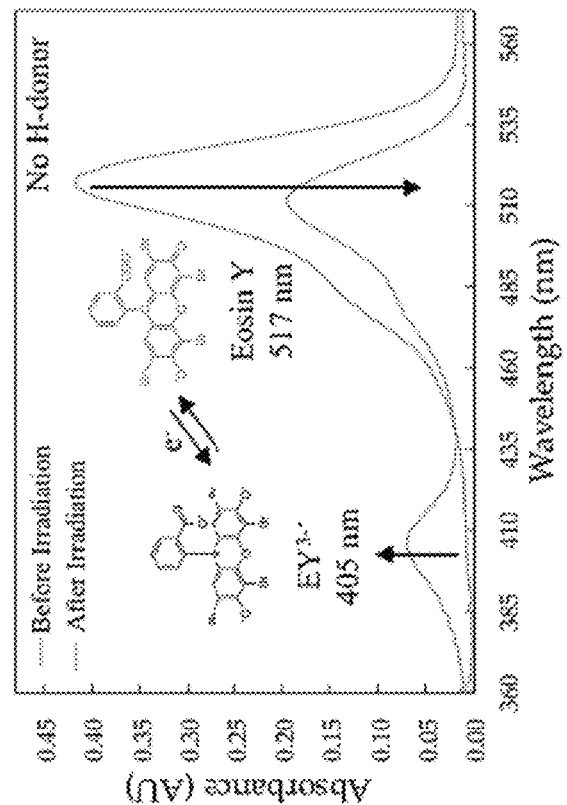
FIG. 2A
FIG. 2B

LIGHT-ASSISTED PHOTOCATALYST REGENERATION AND OXYGEN-RESILIENT RADICAL POLYMERIZATION

CLAIM OF PRIORITY

This application claims the benefit of prior U.S. Provisional Application No. 62/418,247 filed on Nov. 6, 2016, which is incorporated by reference in its entirety.

STATEMENT REGARDING FEDERALLY SPONSORED RESEARCH OR DEVELOPMENT

This invention was made with Government support under Grant No. W81XWH-13-1-0272 awarded by the U.S. Army Medical Research and Material Command. The Government has certain rights in the invention.

TECHNICAL FIELD

This invention relates to photocatalysts.

BACKGROUND

Polymerization and crosslinking reactions initiated by radicals are the most widely implemented method for the synthesis of hydrogels in biomedicine, where physiological oxygen must be present despite inhibiting radical initiation. Eosin Y has gained attention because it enables fast visible-light driven initiation of these reactions in the presence of over one thousand times excess oxygen. However, the reaction mechanism behind the resilience to oxygen remains inconclusive.

SUMMARY

A method of regenerating a photocatalyst can include irradiating the photocatalyst with a first range of wavelengths of light that excite the photocatalyst to one or more intermediates and irradiating the one or more intermediates with a second range of wavelengths of light that turns the intermediate to the photocatalyst.

In certain embodiments, the one or more intermediates can turn to the photocatalyst in the presence of oxygen.

In certain embodiments, the photocatalyst can be in a medium.

In certain embodiments, the medium can be aqueous.

In certain embodiments, the medium can be non-aqueous.

In certain embodiments, the photocatalyst can be Eosin Y.

In certain embodiments, the first range of wavelengths of light can be from 430 nm to 560 nm.

In certain embodiments, the first range of wavelengths of light can be from 516 nm to 525 nm.

In certain embodiments, the second range of wavelengths of light can be from 350 nm to 420 nm.

In certain embodiments, the second range of wavelengths of light can be from 405 nm to 408 nm.

In certain embodiments, a concentration of the photocatalyst in the medium can be 0.1-40 µM.

In certain embodiments, an intensity of the first range of wavelengths of light can be 0.75-35 mW/cm$^2$.

In certain embodiments, the photocatalyst can polymerize or crosslink monomers into a hydrogel.

In another embodiment, a method of diagnose a disease can include preparing a solution including a monomer and a photocatalyst in a medium, adding a body fluid to the solution, irradiating the solution with a first range of wavelengths of light that excite the photocatalyst to one or more intermediates, irradiating the solution with a second range of wavelengths of light that turns the one or more intermediates to the photocatalyst; and diagnosing a disease if the monomer polymerizes.

In certain embodiments, the one or more intermediates can turn to the photocatalyst in the presence of oxygen.

In certain embodiments, the medium can be aqueous.

In another embodiment, a method of fluorescence imaging can include exposing a sample with a fluorophore dye with a first range of wavelengths of light that excite the photocatalyst to one or more intermediates and exposing the sample with a second range of wavelengths of light that turns the one or more intermediates to the photocatalyst.

In certain embodiments, the one or more intermediates can turn to the photocatalyst in the presence of oxygen.

In certain embodiments, the sample can be in a medium.

In certain embodiments, the medium can be aqueous.

In certain embodiments, the one or more intermediates is a single intermediate compound. In other embodiments, the one or more intermediates is a plurality of intermediate compounds.

Other aspects, embodiments, and features will be apparent from the following description, the drawings, and the claims.

BRIEF DESCRIPTION OF THE DRAWINGS

FIGS. 2A-2D show creation and fate of Eosin Y-based intermediates. FIG. 2A shows partially reduced EY.$^{3-}$ (406 nm) is produced during irradiation of an aqueous solution of Eosin Y (517 nm) and triethanolamine (TEOA) in the absence of oxygen. FIG. 2B shows O$_2$ and N-vinylpyrrolidone (NVP) preclude observation of EY.$^{3-}$. FIG. 2C shows the EY.$^{3-}$ peak was not detected upon addition of NVP as a hydrogen donor. Instead, a peak at 308 nm increases as the Eosin Y peak (517 nm) decreases. This peak corresponds to the fully reduced "dead" photocatalyst EY-H$_2$$^{2-}$. FIG. 2D shows the Eosin Y concentration remains fairly constant in the presence of O$_2$ because EY.$^{3-}$ reacts with O$_2$ to regenerate Eosin Y. While O$_2$ oxidizes EY.$^{3-}$ back to Eosin Y, NVP accelerates full reduction of Eosin Y to EY-H$_2$$^{2-}$.

FIG. 3A shows exergonic Eosin Y regeneration competes with full reduction through the acid-base equilibrium of EY.$^{3-}$/EY-H.$^{2-}$. FIG. 3B shows that exposure to violet (405 nm) radiation of oxygenated Eosin Y/TEOA solutions promotes regeneration of Eosin Y photocatalyst during irradiation with a green LED (500 nm).

FIG. 4A shows simultaneous irradiation (10 s) with high intensity green and violet LED resulted in slightly earlier gelation of the PEGDA hydrogels than exposure to the green LED alone, as observed by photos of the two cuvettes upside down under a UV light. FIGS. 4B-4D shows residual Eosin Y and monomer conversion during continuous irradiation of aqueous Eosin Y/triethanolamine/N-vinylpyrrolidone solutions with a green LED (500 nm) in the absence of oxygen (− O$_2$) (FIG. 4B), in the presence of oxygen (+ O$_2$) (FIG. 4C) and in the presence of oxygen and low-intensity violet light (405 nm) (FIG. 4D).

FIG. 19A shows the effect of the presence of superoxide dismutase (SOD) in hydrogen peroxide detection assay. FIG. 19B shows CIELAB color space was used to quantify the differences between samples.

DETAILED DESCRIPTION

Figure 1:
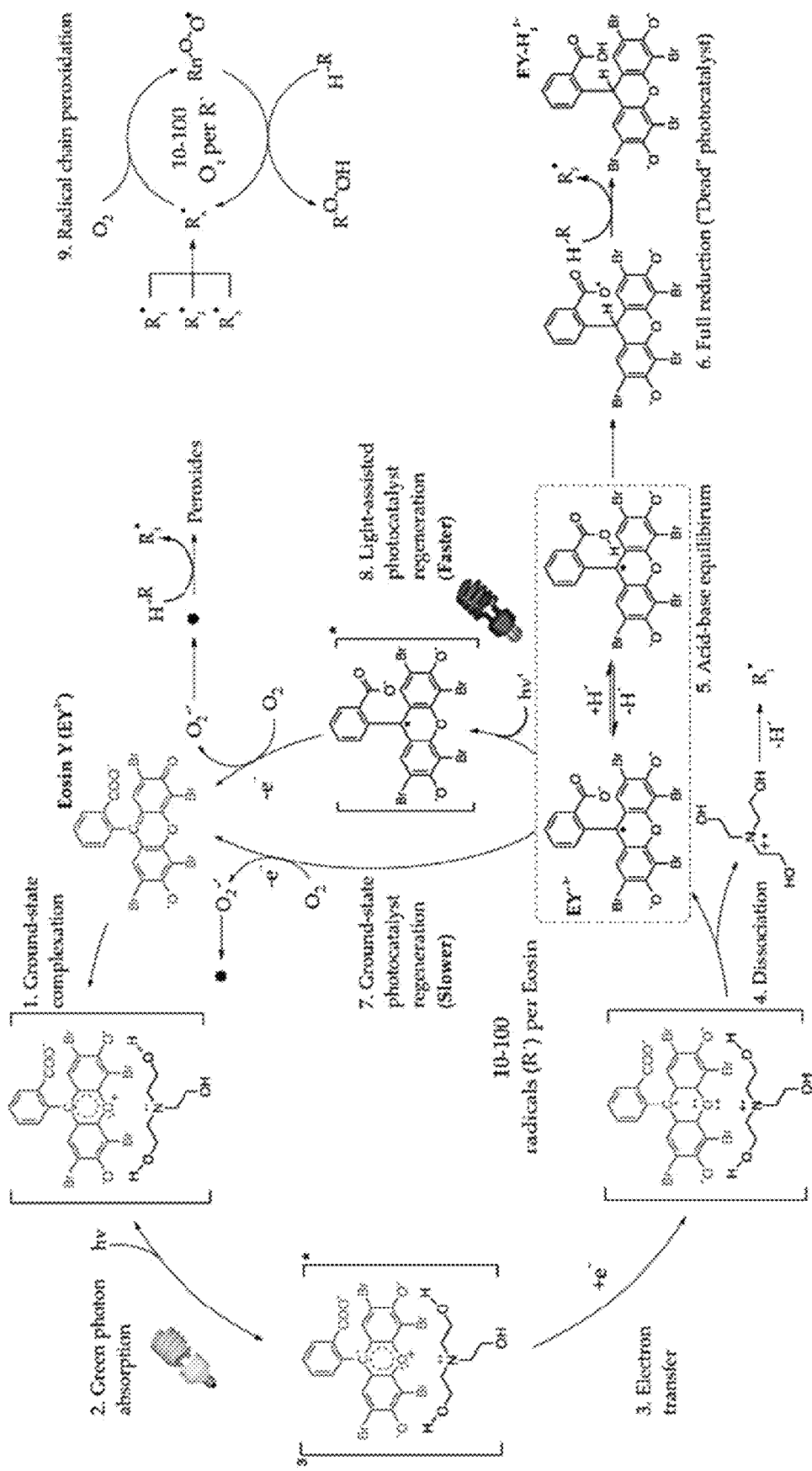
FIG. 1 shows mechanism of light-assisted photocatalyst regeneration.
Figure 2D:
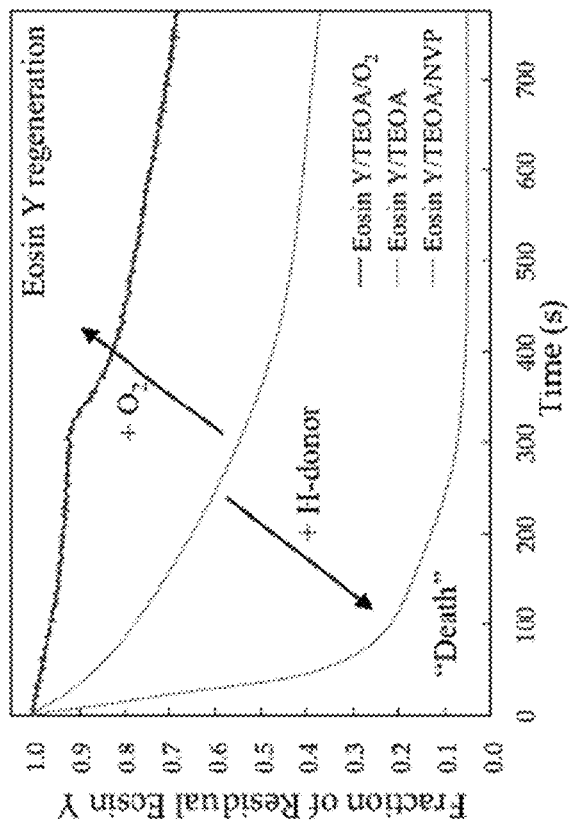
Figure 2C:
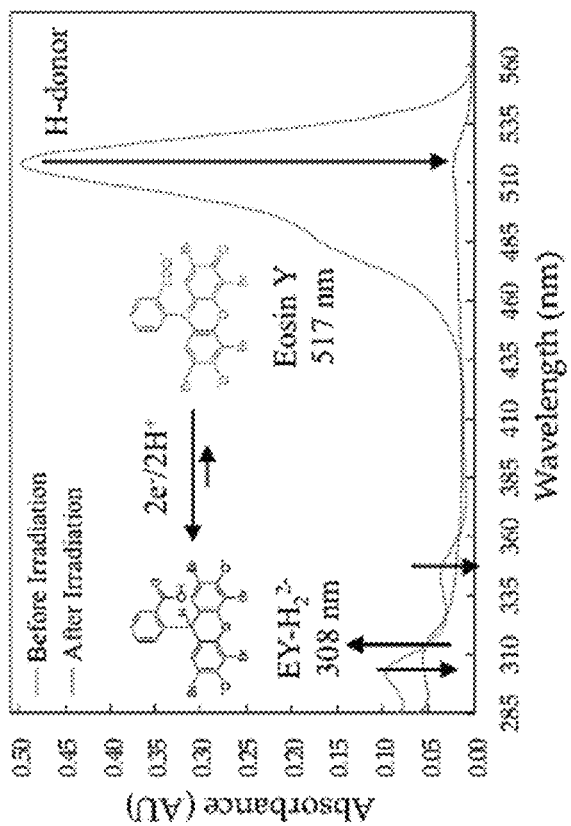

The regeneration of an organic visible-light photocatalyst can be selectively accelerated by light to prevent photocatalyst "death" and enable radical polymerization under excess oxygen. Disclosed herein is a method of regenerating a photocatalyst with increasing efficiency, turnover number and turnover frequency of photo-activated organic catalyst that can be used to form chemical bonds through a radical mechanism in the presence of air. An unexpected metastable intermediate in this reaction pathway can increase efficiency, turnover number and turnover frequency of the catalyst. Increasing efficiency, turnover number and turnover frequency of these catalysts can speed up reactions and increases regeneration yield of the products. These improvements are particularly needed to make organic catalysts competitive with more traditional inorganic catalysts that could have higher selectivity.

A method to regenerate a photocatalyst can include irradiating the photocatalyst with a first range of wavelengths of light that excite the photocatalyst to one or more intermediates and irradiating the one or more intermediates with a second range of wavelengths of light that turns the one or more intermediates to the photocatalyst. The excitation of multiples intermediates is also envisioned. In certain embodiments, the intermediate turns to the photocatalyst in the presence of oxygen. In other words, the regeneration of the photocatalyst effectively consumes oxygen so that the oxygen inhibition issue in free radical photopolymerization reaction can be prevented.

For example, the aqueous photocatalysis of Eosin Y explains the remarkable resilience to oxygen inhibition. Formation of visible-light absorbing metastable intermediates allows the photocatalyst to be regenerated by oxygen. Utilization of light can selectively accelerate photocatalyst regeneration. Light-assisted photocatalyst regeneration feeds radicals to a chain peroxidation process to permit the consumption of thousands of oxygen molecules per Eosin Y. After oxygen depletion, Eosin Y remains available for initiation. Light-assisted photocatalyst regeneration promises to aid in numerous applications, including the synthesis of hydrogels to diagnose and treat diseases.

In addition to the hydrogel synthesis, the method disclosed herein can be applied to energy storage and transfer from light (including sunlight), hydrogen production from water has been achieved with Eosin Y and some co-catalyst in water with triethanolamine as sacrificial reductant, several chemical synthesis methods, the synthesis of pharmaceuticals with specific stereochemistry, the hydrolysis of water for photocatalytic fuel production, chemical oxygen sensors, water treatment, fluorescence microscopy and polymer synthesis, including the visible-light driven atom transfer radical polymerization (ATRP) to make specialty polymers. Increasing the turnover number and turnover frequency of a photocatalyst can useful for the synthesis and transformation of organic molecules.

Previously, mostly broad-spectrum lamps have been used, such as mercury arc lamp and tungsten lamp. For example, the mercury arc lamps have a band around 405 nm, which excites the intermediate of Eosin Y. However, even if the lamps emit at the appropriate wavelengths to excite the intermediates, in most cases they actually passed the light through glass filters. These filters acted like cut-off filters, eliminating all light below a certain wavelength. Also, most of the previous examples removed oxygen. Also, none of the prior examples used the two wavelengths to photo-excite the intermediates as well as the photocatalysts. See, U.S. Pat. Nos. 2,448,828, 2,850,445, 2,875,047, 3,488,269, 3,573,922, 3,615,452, 3,673,375, 4,315,998, 4,772,530, 4,743,531, 4,755,450, 4,842,980, 6,121,341 and U.S. Patent Application Publication No. 2009/0005263, each of which is incorporated by reference in its entirety. Some of the formulations previously disclosed used two compounds for the reaction: 1) a light absorbing compound and 2) a reductant or oxidant. In these cases, even if they had the right wavelengths, the photocatalytic cycle would not be able to complete unless they actually had the three elements: a) photocatalyst, b) reductant, and c) oxidant. None of the prior art used two independent lasers to photo-excite different species.

Disclosed herein, a "photocatalyst" refers to a light absorbing catalyst. In certain embodiments, a photocatalyst is a photo-activated organic catalyst. In certain embodiments, the photocatalyst can be Eosin Y. Preferably, a concentration of Eosin Y can range from 0.3 µM to 40 µM. Wavelength (envelope) of light absorption of a photocatalyst can range from 450 to 850 nm. Wavelength (envelope) of light absorption of an intermediate can range from 350 to 500 nm. In certain embodiments, wavelength (frequency) used for the excitation of a photocatalyst can be 500 nm or 530 nm. In certain embodiments, wavelength (frequency) used for the excitation of the intermediate can be 405 nm. In certain embodiments, irradiance (intensity) of light sources used for the excitation of both the photocatalyst and the intermediate can be 0.75-35 mW/cm$^2$. In certain embodiments, types of light sources can be monochromatic or panchromatic (such as light-emitting diodes, lasers, mercury lamps, sunlight) and pulsed or continuous irradiation. This method can use either one photon or two photon absorption, i.e. stereolithographic systems can operate by either excitation approach. This method can be used in aqueous or non-aqueous medium. For example, an aqueous medium can be used for synthesis of hydrogels.

The general principal of the disclosed method can extend to all chromophores that can be reduced or oxidized when excited to a singlet or a triplet state from which one or more redox species (light-absorbing transients) are produced, as for example semireduced (half-reduced or semiquinone) or semioxidized transient species, where the semiquinone transients are more suitable for visible-light excitation, but the leuco form of the chromophore(s) could also be photo-activated in the same manner by appropriate wavelength selection. Extension to other chemistries is supported by the principle that semiquinones are ubiquitous transients (intermediates) in reversible organic oxidation-reduction reaction. See, L. Michaelis, semiquinones, the intermediate steps of reversible organic oxidation-reduction. *Chemical Reviews*, 16, 243-286, (1935), which is incorporated by reference in its entirety. Other types of intermediates are also possible.

A promising direct application of the light-assisted chromophore regeneration is fluorescence microscopy where a wide range of so-called fluorophores are dyes with the same core as the chromophoric cores described herein, e.g. Atto, Alexa and Cy fluorophores family. One of the major problems in this application is the so-called "photobleaching" or "photostability" of the fluorophores dyes. This invention can provide a method to prevent "photobleaching" of any fluorophores dye, where the imaging optical systems are already equipped with the optomechanical and optoelectronical systems to control the exposure of the samples to multiple wavelengths (frequencies) simultaneously at controlled intensities, but where the precise matching of those wavelengths with the intermediates of the "photobleaching" processes has never been reported. Additional software and methods and adaptations are needed to expose the fluorophores dyes to the precise doses of the correct wavelengths to sustain its concentration for longer exposure times without altering the imaging results. To date there is no direct method to reduce "photobleaching". Hence, the field has relied on development of new fluorophores molecular structures with higher quantum yields of fluorescence and lower quantum yields of intersystem crossing, electron and energy transfer processes, for these are the typical culprits for the "photobleaching" of the dyes (staining molecules).

Another promising application is the synthesis of pharmaceutical compounds, including through visible light oxidative C—C, C—P, C—O, C—N or C—S bond formation reactions, in batch, semibatch, or continuous photoreactors. Examples include, but are not limited to enantioselective alkylation of aldehydes, cycloadditions ([2+2], [4+2], [2+2+2], [3+2], CuAAC), thiol-ene, thiol-yne, Reductive radical cyclizations of aryl, alkyl and alkenyl iodides, reductive pinacol coupling of aldehydes and ketones, Oxidative deprotection of para-methoxybenzyl (PMB) ethers, atom-transfer radical addition, and Diels-Alder. Other types and classes of reactors are also possible. A combination of light sources can be used to photoexcite the reactant solution with appropriate wavelengths at appropriate intensities to selectively favor one synthetic pathway over other pathways. This is advantageous when highly reactive intermediates are produced, where several reactions are feasible, some of which may be undesired. The kinetics of the multiple reaction pathways can be then tuned by light to reduce the yields of the undesired reactions and selectively increase the yield of the desired pathway. By appropriate selection of a photocatalyst/reductant/oxidant/light source(s) combination one can then selectively synthesize molecules that are not accessible by other routes. This is primarily interesting for cases of stereoisomers and enantioselective transformations utilized in the pharmaceutical industry.

In certain embodiments, the light-absorbing molecules (photocatalysts) can include xanthene dyes (fluorescein derivatives), such as Eosin Y, Eosin B, Rose Bengal, Erythrosine B, Fluorescein and its derivatives, Phloxin, Fluorone dyes, and Rhodamine dyes (Rhodamine 6G, Rhodamine B, Rhodamine 123, Alexa family). These dyes have a xanthene (fluorone) core. The critical wavelengths of certain examples are as follows:

| Dye | Photocatalyst excitation (nm) | Intermediate excitation (nm) |
| --- | --- | --- |
| Eosin Y | 430-560 | 350-420[a] |
| Eosin B | 430-560 | 380-420[b] |
| Rose Bengal | 500-600 | 400-480[a] |
| Fluorescein | 420-530 | 350-410 |

[a]R. F. Bartholomew, R. S. Davidson, The photosensitized oxidation of amines. Part II. The use of dyes as photosensitizers: Evidence that singlet oxygen is not involved. *J. Chem. Soc. Part C*, 2347-2351, (1971), which is incorporated by reference in its entirety.
[b]By analogy with Eosin Y.

In certain embodiments, the light-absorbing molecules (photocatalysts) can include phenothiazine (phenotiazinium) dyes, such as Methylene Blue, New Methylene Blue, Thionine, Azure B, promethiazine, and others. These dyes have a phenothiazine core. The critical wavelengths of certain examples are as follows:

| Dye | Photocatalyst excitation (nm) | Intermediate excitation (nm) |
| --- | --- | --- |
| Methylene Blue | 550-700 | 350-500[a, c] & 520[c] |
| New Methylene Blue | 500-700 | 300-700 |
| Thionine | 500-650 | 300-700 |
| Azure B | 550-700 | 300-700 |

[a]R. F. Bartholomew, R. S. Davidson, The photosensitized oxidation of amines. Part II. The use of dyes as photosensitizers: Evidence that singlet oxygen is not involved. *J. Chem. Soc. Part C*, 2347-2351, (1971), which is incorporated by reference in its entirety.
[c]S. Kato, M. Morita, M. Koizumi, Studies of the transient intermediates in the photoreduction of Methylene Blue, Bulletin of the Chemical Society of Japan, 37, 117-124, (1964), which is incorporated by reference in its entirety.

In certain embodiments, the light-absorbing molecules (photocatalysts) can include aromatic ketones, such as benzophenone. The critical wavelengths of certain examples are as follows:

| Chromophore | Photocatalyst excitation (nm) | Intermediate excitation (nm) |
|---|---|---|
| Benzophenone | 350 | 340-700[d] |

[d]S. G. Cohen, H. M. Chao, Photoreduction of aromatic ketones by amines. Studies of quantum yields and mechanism. *Journal of the American Chemical Society*, 90, 165-173, (1971), which is incorporated by reference in its entirety.

In certain embodiments, the light-absorbing molecules (photocatalysts) can include Acridine dyes, such as acridine, acridine orange and acridine yellow. These dyes have an acridine core. The critical wavelengths of certain examples are as follows:

| Chromophore | Photocatalyst excitation (nm) | Intermediate excitation (nm) |
|---|---|---|
| Anthracene* | 300-390 | 400-420[e] |
| Acridine | 300-420 | 400-550[f, g] |
| Acridine orange | 340-510 | 350-700 |
| Acridine yellow | 330-500 | 350-720[e] |
| Acridone | 350-400[h] | 500-600[h] |

*Anthracene is included with the acridines as comparisons have been made amongst these in the literature to evaluate the effect of making the core a heterocycle.
[e]H. Masuhara, M. Okuda, M. Koizumi, Studies on the electronic spectra of the semiquinones of Anthracene and its related heterocycles. I. *Bulletin of the Chemical Society of Japan.* 43, 2319-2324, (1968), which is incorporated by reference in its entirety.
[f]A. Kira, Y. Ikeda, M. Koizumi, Reactive species in the photochemical hydrogenation of acridine in ethanol. *Bulletin of the Chemical Society of Japan.* 39, 1673-1678, (1966), which is incorporated by reference in its entirety.
[g]A. Kira, S. Kato, M. Koizumi, Studies of the photoreduction of acridine in ethanol by the flash technique. *Bulletin of the Chemical Society of Japan.* 39, 1221-1227, (1966), which is incorporated by reference in its entirety.
[h]S. Niizuma, H. Kawata, CIDEP study of radicals produced photochemically in the organic solution of 9-acridone and phenols. *Bulletin of the Chemical Society of Japan.* 66, 1627-1632, (1993), which is incorporated by reference in its entirety.

In certain embodiments, the light-absorbing molecules (photocatalysts) can include Pyronin derivatives. These dyes have a pyronin core. The critical wavelengths of certain examples are as follows:

| Dye | Photocatalyst excitation (nm) | Intermediate excitation (nm) |
|---|---|---|
| Thiopyronine | 500-620 | 350-500[i] |

[i]M. Morita, S. Kato, Studies of the transient intermediates of a thiopyronine aqueous solution under flash excitation. *Bulletin of the Chemical Society of Japan.* 42, 25-35, (1969), which is incorporated by reference in its entirety.

In certain embodiments, the light-absorbing molecules (photocatalysts) can include Aporphine dyes, such as aporphine and 2,3-dihydro-oxoisoaporphine. These dyes have an aporphine core. The critical wavelengths of certain examples are as follows:

| Dye | Photocatalyst excitation (nm) | Intermediate excitation (nm) |
|---|---|---|
| 2,3-dihydro-oxoisoaporphine | 350-520[j] | 400-500 & 400-550[j] |

[j]J. R. De la Fuente, V. Neira, C. Saitz, C. Jullian, E. Sobarzo-Sanchez, Photoreduction of Oxoisoaporphine Dyes by Amines: Transient-Absorption and Semiempirical Quantum-Chemical Studies. *J. Phys. Chem. A*, 109, 5897-5804, (2005), which is incorporated by reference in its entirety.

In certain other embodiments, the light-absorbing molecules (photocatalysts) can include Coumarine dyes, Anthraquinone dyes, Arylmethane dyes, Azo dyes, Diazonium dyes, Nitro dyes, Nitroso dyes, Phtalocyanine dyes, Quinone-imine dyes, Thiazole dyes, Safranin dyes, Cyanine dyes (e.g. cyanine borate, Cy family of fluorescent dyes), Phenoxazines, Phenosafranins, Squarylium, or Fluorenone dyes.

The phenomenal properties of hydrogels have led to important advances in biology, biomedicine and bioengineering, including contact lenses, drug delivery, cell encapsulation, 3D printing, tissue engineering, soft robotics, biosensing, and regenerative medicine. See, N. A. Peppas, J. Z. Hilt, A. Khademhosseini, R. Langer, Hydrogels in biology and medicine: From molecular principles to bionanotechnology. *Adv. Mater.* 18, 1345-1360 (2006), R. M. Ottenbrite, K. Park, T. Okano, *Biomedical Applications of Hydrogels Handbook* (Springer Science & Business Media, New York, N.Y., 2010), X. Du, J. Zhou, J. Shi, B. Xu, Supramolecular hydrogelators and hydrogels: From soft matter to molecular biomaterials. *Chem. Rev.* 115, 13165-13307 (2015), P. C. Nicolson, J. Vogt, Soft contact lens polymers: An evolution. *Biomaterials.* 22, 3273-3283 (2001), N. A. Peppas, P. Bures, W. Leobandung, H. Ichikawa, Hydrogels in pharmaceutical formulations. *Eur J Pharm Biopharm.* 50, 27-46 (2000), A. S. Sawhney, C. P. Pathak, J. A. Hubbell, Interfacial photopolymerization of poly (ethylene glycol)-based hydrogels upon alginate-poly (1-lysine) microcapsules for enhanced biocompatibility. *Biomaterials.* 14, 1008-1016 (1993), L. A. Hockaday, K. H. Kang, N. W. Colangelo, P. Y. C. Cheung, B. Duan, E. Malone, J. Wu, L. N. Girardi, L. J. Bonassar, H. Lipson, C. C. Chu, J. T. Butcher, Rapid 3D printing of anatomically accurate and mechanically heterogeneous aortic valve hydrogel scaffolds. *Biofabrication.* 4, 035005- (2012), C. A. DeForest, D. A. Tirrell, A photoreversible protein-patterning approach for guiding stem cell fate in three-dimensional gels. *Nature Materials.* 14, 523-531 (2015), S. A. Morin, R. F. Shepherd, S. W. Kwok, A. A. Stokes, A. Nemiroski, G. M. Whitesides, Camouflage and display for soft machines. *Science.* 337, 828-832 (2012), H. D. Sikes, R. R. Hansen, L. M. Johnson, R. Jenison, J. W. Birks, K. L. Rowlen, C. N. Bowman, Using polymeric materials to generate an amplified response to molecular recognition events. *Nature Materials.* 7, 52-56 (2007), and B. V. Slaughter, S. S. Khurshid, O. Z. Fisher, A. Khademhosseini, N. A. Peppas, Hydrogels in regenerative medicine. *Adv. Mater.* 21, 3307-3329 (2009), each of which is incorporated by reference in its entirety. By far, the most practical and efficient method to synthesize hydrogels is initiating polymerization and crosslinking reactions with radicals. See, N. A. Peppas, J. Z. Hilt, A. Khademhosseini, R. Langer, Hydrogels in biology and medicine: From molecular principles to bionanotechnology. *Adv. Mater.* 18, 1345-1360 (2006), and E. H. Schacht, Polymer chemistry and hydrogel systems. *J. Phys.: Conf. Ser.* 3, 22-28 (2004), each of which is incorporated by reference in its entirety. However, clinical translation has been hindered by the challenge of forming hydrogels under physiological conditions, including the presence of oxygen inhibitor. See, G. Gerlach, K. F. Arndt, *Hydrogel Sensors and Actuators* (Springer Science & Business Media, Berlin, Heidelberg, 2009), vol. 6, and S. C. Ligon, B. Husár, H. Wutzel, R. Holman, R. Liska, Strategies to reduce oxygen inhibition in photoinduced polymerization. *Chem. Rev.* 114, 557-589 (2014), each of which is incorporated by reference in its entirety. Although several chemistries have been implemented, they require reagents or energy doses that may reasonably be expected to introduce unwanted perturbations to proteins, cells, tissues and organisms. See, C. G. Williams, A. N. Malik, T. K. Kim, P. N. Manson, J. H. Elisseeff, Variable cytocompatibility of six cell lines with photoinitiators used for polymerizing hydrogels and cell encapsulation. 26, 1211-1218 (2005), which is incorporated by reference in its entirety. Organic photoredox catalysis has garnered attention as a benign alternative to initiate radical polymerizations in the presence of oxygen under mild conditions. See, P. Xiao, J. Zhang, F. Dumur, M. A. Tehfe, F. Morlet-Savary, B. Graff, D. Gigmes, J. P. Fouassier, J. Lalevée, Visible light sensitive photoinitiating systems: Recent progress in cationic and radical photopolymerization reactions under soft conditions. *Progress in Polymer Science.* 41, 32-66 (2015), which is incorporated by reference in its entirety. Eosin Y photocatalyst is particularly exceptional at forming hydrogels against more than a thousand times excess oxygen at ambient temperature under mild radiation for short times. See, A. S. Sawhney, C. P. Pathak, J. A. Hubbell, Interfacial photopolymerization of poly (ethylene glycol)-based hydrogels upon alginate-poly (1-lysine) microcapsules for enhanced biocompatibility. *Biomaterials.* 14, 1008-1016 (1993), L. Kuck, A. Taylor, Photopolymerization as an innovative detection technique for low-density microarrays. *Biotech.* 45, 179-186 (2008), and H. J. Avens, C. N. Bowman, Mechanism of cyclic dye regeneration during eosin-sensitized photoinitiation in the presence of polymerization inhibitors. *J. Polym. Sci. A Polym. Chem.* 47, 6083-6094 (2009), each of which is incorporated by reference in its entirety. However, the mechanism behind the impressive resilience to oxygen inhibition remains inconclusive, as for many photocatalysis systems. See, H. J. Avens, C. N. Bowman, Mechanism of cyclic dye regeneration during eosin-sensitized photoinitiation in the presence of polymerization inhibitors. *J. Polym. Sci. A Polym. Chem.* 47, 6083-6094 (2009), N. Corrigan, S. Shanmugam, J. Xu, C. Boyer, Photocatalysis in organic and polymer synthesis. *Chem. Soc. Rev.,* 1-48 (2016), and N. Corrigan, S. Shanmugam, J. Xu, C. Boyer, Photocatalysis in organic and polymer synthesis. *Chem. Soc. Rev.,* 1-48 (2016), each of which is incorporated by reference in its entirety. In an effort to elucidate this mechanism, the Eosin Y regeneration was accelerated by light. Here, light-assisted photocatalyst regeneration was introduced as a tool to aid in the implementation of organic visible-light photocatalysis, especially for hydrogel synthesis in the presence of atmospheric or physiological oxygen.

While numerous investigations have centered on the photochemistry of Eosin Y, few have attempted to elucidate the mechanism by which Eosin Y initiates radical polymerization in the presence of oxygen. See, G. Oster, A. H. Adelman, Long-Lived states in photochemical reactions. I. Photoreduction of Eosin. *J. Am. Chem. Soc.* 78, 913-916 (1956), J. S. Bellin, G. Oster, Photoreduction of Eosin in the bound state1a, b. *J. Am. Chem. Soc.* (1957), Y. Usui, K. Itoh, M. Koizumi, Switch-over of the mechanism of the primary processes in the photo-oxidation of xanthene dyes as revealed by the oxygen consumption experiments. *Bull. Chem. Soc. Jpn.* 38, 1015-1022 (1965), V. Kasche, L. Lindqvist, Transient species in the photochemistry of eosin. *Photochem Photobiol.* 4, 923-933 (1965), E. Chesneau, J. P. Fouassier, Polymérisation induite sous irradiation laser visible. 2. Sensibilisation par les colorants. *Die Angewandte Makromolekulare Chemie.* 135, 41-64 (1985), J. P. Fouassier, E. Chesneau, M. LeBaccon, Polymérisation induite sous irradiation laser visible, 3. Un nouveau système photosensible performant. *Die Makromolekulare Chemie, Rapid Communications.* 9, 223-227 (1988), J. P. Fouassier, E. Chesneau, Polymerisation induite sous irradiation laser visible, 4. Le système éosine/photoamorceur ultra-violet/amine. *Die Makromolekulare Chemie.* 192, 245-260 (1991), J. P. Fouassier, E. Chesneau, Polymérisation induite sous irradiation laser visible, 5. Le système éosine/amine/sel de iodonium. *Die Makromolekulare Chemie.* 192, 1307-1315 (1991), J. Wong, K. Kaastrup, A. Aguirre-Soto, H. D. Sikes, A quantitative analysis of peroxy-mediated cyclic regeneration of eosin under oxygen-rich photopolymerization conditions. *Polymer.* 69, 169-177 (2015), J. Wong, H. D. Sikes, The impact of continuous oxygen flux in a thin film photopolymerization reaction with peroxy-mediated regeneration of initiator. *Macromolecular Theory and Simulations.* 25, 229-237 (2016), K. Kaastrup, A. Aguirre-Soto, C. Wang, C. N. Bowman, J. W. Stansbury, H. D. Sikes, UV-Vis/FT-NIR in situ monitoring of visible-light induced polymerization of PEGDA hydrogels initiated by eosin/triethanolamine/O 2. *Polym. Chem.* 7, 592-602 (2016), and H. J. Avens, C. N. Bowman, Mechanism of cyclic dye regeneration during eosin-sensitized photoinitiation in the presence of polymerization inhibitors. *J. Polym. Sci. A Polym. Chem.* 47, 6083-6094 (2009), each of which is incorporated by reference in its entirety. Oster discovered that $O_2$ is often required for significant polymerization to occur, and Delzenne reported the first evidence of Eosin Y regeneration in the presence of $O_2$. See, G. Oster, Dye-Sensitized photopolymerization. *Nature.* 173, 300-301 (1954), and G. Delzenne, S. Toppet, G. Smets, Photopolymerization of acrylamide. I. Formation of the initiating redox system. *J. Polym. Sci.* 48, 347-355 (1960), each of which is incorporated by reference in its entirety. Later, Fouassier and coworkers proposed a mechanism where Eosin Y is reduced by an amine via hydrogen ($e^-/H^+$) transfer to form intermediates that convert back to Eosin Y by reaction with $O_2$ and peroxy radicals, produced from radical quenching by oxygen, i.e. inhibition, in non-polar aprotic monomers. See, E. Chesneau, J. P. Fouassier, Polymérisation induite sous irradiation laser visible. 2. Sensibilisation par les colorants. *Die Angewandte Makromolekulare Chemie.* 135, 41-64 (1985), which is incorporated by reference in its entirety. Avens et al. then postulated that such a mechanism could explain the outstanding resilience to $O_2$ inhibition during hydrogel formation. See, H. J. Avens, C. N. Bowman, Mechanism of cyclic dye regeneration during eosin-sensitized photoinitiation in the presence of polymerization inhibitors. *J. Polym. Sci. A Polym. Chem.* 47, 6083-6094 (2009), which is incorporated by reference in its entirety. Kinetic modeling led us to conclude that Eosin Y regeneration by peroxy radicals is plausible, but appears insufficient to explain the resilience to oxygen inhibition. Se, J. Wong, K. Kaastrup, A. Aguirre-Soto, H. D. Sikes, A quantitative analysis of peroxy-mediated cyclic regeneration of eosin under oxygen-rich photopolymerization conditions. *Polymer.* 69, 169-177 (2015), and J. Wong, H. D. Sikes, The impact of continuous oxygen flux in a thin film photopolymerization reaction with peroxy-mediated regeneration of initiator. *Macromolecular Theory and Simulations.* 25, 229-237 (2016), each of which is incorporated by reference in its entirety. Then, it was confirmed that Eosin Y does regenerate when $O_2$ is present in water, but suggested that regeneration and resilience to $O_2$ inhibition appeared to be associated with a primary photochemical process from the triplet Eosin Y. See, K. Kaastrup, A. Aguirre-Soto, C. Wang, C. N. Bowman, J. W. Stansbury, H. D. Sikes, UV-Vis/FT-NIR in situ monitoring of visible-light induced polymerization of PEGDA hydrogels initiated by eosin/triethanolamine/O 2. *Polym. Chem.* 7, 592-602 (2016), which is incorporated by reference in its entirety. Here, it is proposed that the resilience to $O_2$ inhibition is rooted in the formation of a semireduced radical trianion ($EY^{3-}$) that can donate one electron to $O_2$, converting back to Eosin Y dianion ($EY^{2-}$).

While $EY^{3-}$ has been detected in the photoreduction of Eosin Y, including with amines, its role in $O_2$ depletion and polymerization has been overlooked. See, V. Kasche, L. Lindqvist, Transient species in the photochemistry of eosin. *Photochem Photobiol.* 4, 923-933 (1965), J. Zhang, L. Sun, T. Yoshida, Spectroelectrochemical studies on redox reactions of eosin Y and its polymerization with Zn2+ ions. *Journal of Electroanalytical Chemistry.* 662, 384-395 (2011), A. Goux, T. Pauporté, D. Lincot, L. Dunsch, In situ ESR and UV/vis spectroelectrochemical study of eosin Y upon reduction with and without Zn(II) ions. *Chemphyschem.* 8, 926-931 (2007), Z. G. Zhao, H. J. Xu, T. Shen, D. W. Chen, Effect of pH on the photosensitizing ability of eosin—an intermediate study. *Journal of Photochemistry and Photobiology A:* . . . 56, 73-80 (1991), S. Kizilel, V. H. Perez-Luna, F. Teymour, Photopolymerization of poly(Ethylene Glycol) diacrylate on eosin-functionalized surfaces. *Langmuir.* 20, 8652-8658 (2004), G. M. Cruise, 0. D. Hegre, D. S. Scharp, J. A. Hubbell, A sensitivity study of the key parameters in the interfacial photopolymerization of poly(ethylene glycol) diacrylate upon porcine islets. *Biotechnol. Bioeng.* 57, 655-665 (1998), and D. C. Neckers, O. M. Valdes-Aguilera, in *Advances in Photochemistry* (Adv Photochem, 1993), vol. 18, each of which is incorporated by reference in its entirety. This stems from the generalization that organic photoreductions are hydrogen ($e^-/H^+$) transfer reactions, where a proton ($H^+$) is transferred after electron transfer and before dissociation of the solvated ion pair. However, it has been demonstrated that visible-light absorbing metastable intermediates like $EY.^{3-}$ can be found dissociated in their unprotonated form. See, Y. Usui, K. Itoh, M. Koizumi, Switch-over of the mechanism of the primary processes in the photo-oxidation of xanthene dyes as revealed by the oxygen consumption experiments. *Bull. Chem. Soc. Jpn.* 38, 1015-1022 (1965), and V. Kasche, L. Lindqvist, Transient species in the photochemistry of eosin. *Photochem Photobiol.* 4, 923-933 (1965), each of which is incorporated by reference in its entirety. This led us to investigate the creation and faith of Eosin Y intermediates during visible-light-mediated hydrogel synthesis by coupled electronic and vibrational spectroscopy. From deductive experiments guided by first-principles a mechanism where $EY.^{3-}$ is found in its dissociated form is proposed, allowing direct regeneration of Eosin Y by $O_2$ (FIG. 1), and its role is described in the light-assisted photocatalyst regeneration and the resilience to oxygen inhibition.

FIG. 1 shows mechanism of light-assisted photocatalyst regeneration. An electron-donor-acceptor complex is formed between Eosin Y and triethanolamine (TEOA) in water (Step 1). This ground state charge transfer complex absorbs a green photon (530 nm) in Step 2. Eosin Y is then photo reduced by TEOA (Step 3), where dissociated $EY^{3.-}$ is produced by either 1) dissociation of the $EY^{3.-}$ and $TEOA.^+$ radical ions (Step 4) before protonation of $EY^{3.-}$, or by an acid-base equilibrium of the protonated $EY\text{-}H.^{2-}$ (Step 5) after dissociation. $EY^{3.-}$ readily reacts with $O_2$, converting back to Eosin Y and reducing $O_2$ to superoxide. Intramolecular hydrogen abstraction in $EY\text{-}H.^{2-}$ and subsequent $e^-/H^+$ transfer can occur. Full reduction of the protonated $EY\text{-}H.^{2-}$ intermediate (Step 6) competes with Eosin Y regeneration (Step 7). If $EY\text{-}H.^{2-}$ is fully reduced ($+e^-/H^+$), it becomes difficult to oxidize back to Eosin Y, and is therefore considered "dead" photocatalyst. However, Eosin Y regeneration can be accelerated by photo-excitation of $EY^{3.-}$ by absorption of a violet photon (405 nm), as shown in Step 8. Light-assisted photocatalyst regeneration maintains the Eosin Y concentration constant while $O_2$ is present while producing reactive radicals. A radical chain peroxidation process accelerates oxygen consumption, i.e. thousands of $O_2$ molecules per Eosin Y, before polymerization begins. Thus, light-assisted photocatalyst regeneration ensures 100% of the photocatalyst is available for polymerization after oxygen depletion.

The photoreduction of the excited state triplet of Eosin Y ($^3EY^{2-*}$) by triethanolamine (TEOA) leads to the formation of the expected visible-light absorbing $EY.^{3-}$ intermediate (FIGS. 2A, 2B, 5 and 6) via a loosely bound electron-donor-acceptor complex (FIG. 7), as shown in FIG. 1—Steps 1-3. Whether $EY.^{3-}$ protonates before or after dissociation of the solvated ion pair (FIG. 1—Step 4) (see S. G. Cohen, A. Parola, G. H. Parsons Jr, Photoreduction by amines. *Chem. Rev.* 73, 141-161 (1973), and S. Hammes-Schiffer, Theory of proton-Coupled electron transfer in energy conversion processes. *Acc. Chem. Res.* 42, 1881-1889 (2009), each of which is incorporated by reference in its entirety), $EY.^{3-}$ is finally in its dissociated form because of the acid-base equilibrium of the metastable $EY.^{3-}/EY\text{-}H.^{2-}$ intermediates (FIG. 1—Step 5 and FIG. 8) (see J. Zhang, L. Sun, T. Yoshida, Spectroelectrochemical studies on redox reactions of eosin Y and its polymerization with Zn2+ ions. *Journal of Electroanalytical Chemistry.* 662, 384-395 (2011), A. Goux, T. Pauporté, D. Lincot, L. Dunsch, In situ ESR and UV/vis spectroelectrochemical study of eosin Y upon reduction with and without Zn(II) ions. *Chemphyschem.* 8, 926-931 (2007), and Z. G. Zhao, H. J. Xu, T. Shen, D. W. Chen, Effect of pH on the photosensitizing ability of eosin—an intermediate study. *Journal of Photochemistry and Photobiology A:* . . . 56, 73-80 (1991), each of which is incorporated by reference in its entirety). While it is known that many photoredox reactions are pH dependent, it is surprising that the acid-base equilibrium of photoredox intermediates has not been considered in the mechanisms reported to date. Detection of $EY.^{3-}$ in oxygen-free Eosin Y/TEOA solutions supports the metastability of the $EY.^{3-}/EY\text{-}H.^{2-}$ intermediates (FIG. 9). See, J. Zhang, L. Sun, T. Yoshida, Spectroelectrochemical studies on redox reactions of eosin Y and its polymerization with Zn2+ ions. *Journal of Electroanalytical Chemistry.* 662, 384-395 (2011), which is incorporated by reference in its entirety. This acid-base equilibrium of the metastable photoredox intermediates enables unprecedented control of the rate of photocatalyst regeneration and radical production with light.

Figure 3A:
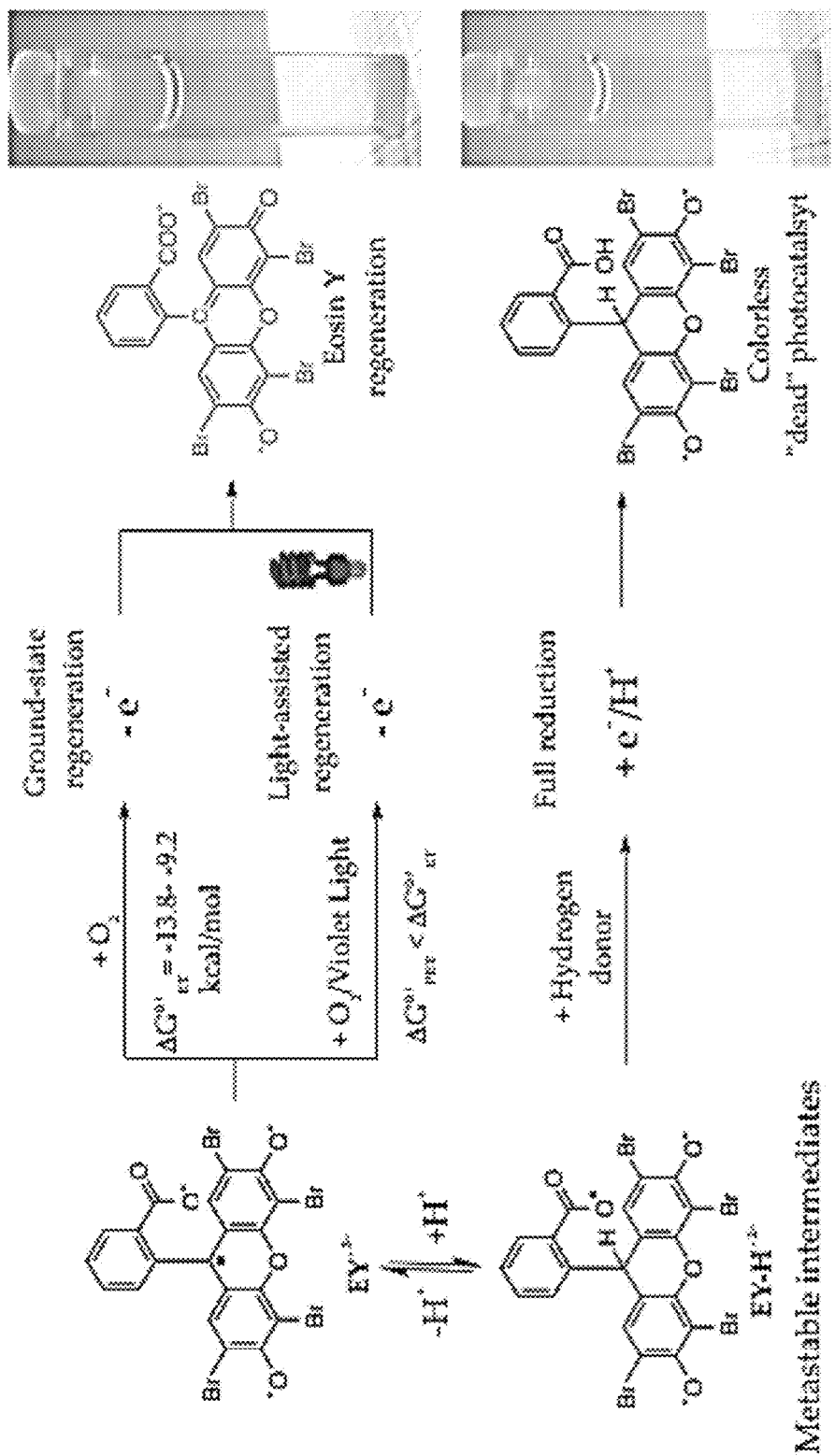
FIGS. 3A-3B show evidence of light-assisted photocatalyst regeneration.
Figure 13:
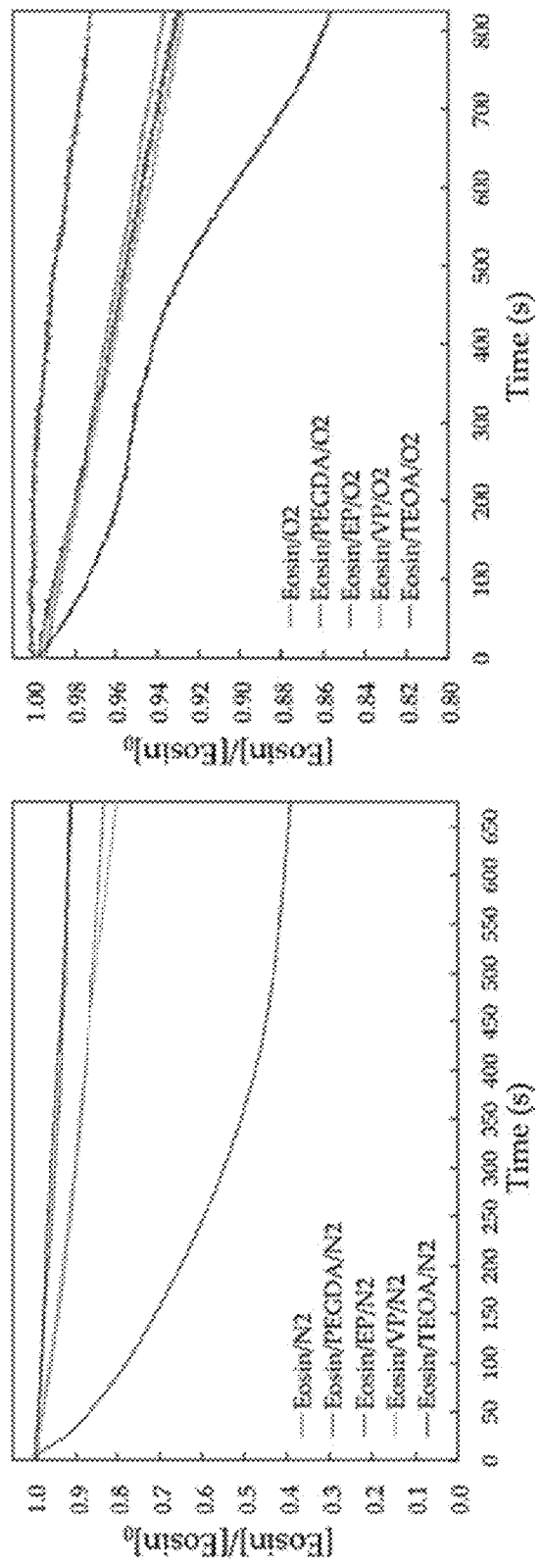
FIG. 13 shows standard free energy change for electron transfer ($\Delta G_{ET}°$) and photoinduced electron transfer ($\Delta G_{PET}°$) and associated kinetic results for consumption of Eosin Y.
Figure 14:
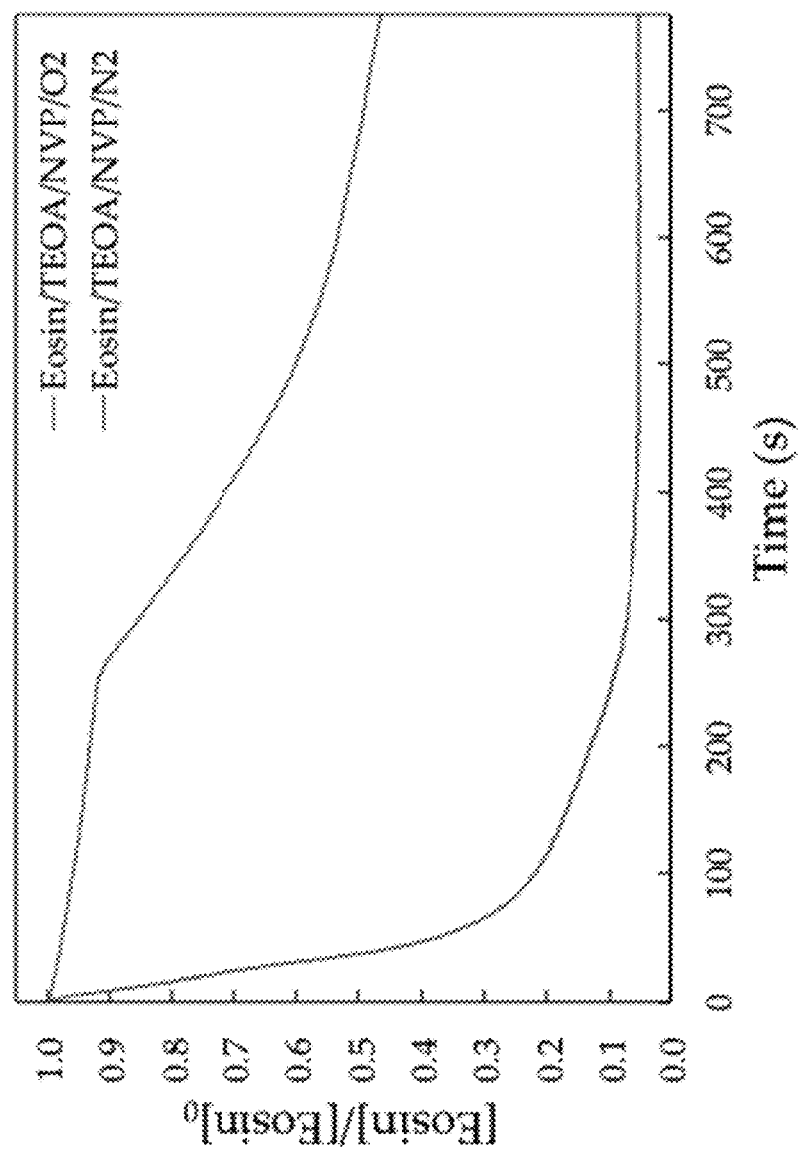
FIG. 14 shows steady-stated spectroscopy of the photoreduction of Eosin Y by TEOA in the presence of N-vinylpyrrolidone (NVP) with and without oxygen and exposed to both violet (405 nm) and green (500 nm) light.

Two ground-state reactions occur from the acid-base equilibrium of the $EY.^{3-}/EY\text{-}H.^{2-}$ metastable intermediates. Hydrogen abstraction from NVP to $EY\text{-}H.^{2-}$ leads to photocatalyst "death" (FIG. 1—Step 6), while electron transfer from $EY.^{3-}$ to $O_2$ regenerates Eosin Y (FIG. 1—Step 7). On one hand, N-vinylpyrrolidone (NVP) precluded detection of $EY.^{3-}$ and increased the rate of Eosin Y consumption dramatically (FIGS. 2B-2D and 9). In contrast, $O_2$ also consumed $EY.^{3-}$, but regenerated Eosin Y as a result (FIGS. 2B-2D and 10). While "dead" photocatalyst $EY\text{-}H_2^{2-}$ (FIGS. 2C and 11) is difficult to oxidize back to Eosin Y (FIG. 12) (see J. Zhang, L. Sun, T. Yoshida, Spectroelectrochemical studies on redox reactions of eosin Y and its polymerization with Zn2+ ions. *Journal of Electroanalytical Chemistry.* 662, 384-395 (2011), which is incorporated by reference in its entirety), Eosin Y regeneration by ground-state electron transfer from $EY.^{3-}$ to $O_2$ is exergonic (FIGS. 10 and 13) (see V. Kasche, L. Lindqvist, Transient species in the photochemistry of eosin. *Photochem Photobiol.* 4, 923-933 (1965), G. Oster, Dye-Sensitized photopolymerization. *Nature.* 173, 300-301 (1954), S. G. Cohen, A. Parola, G. H. Parsons Jr, Photoreduction by amines. *Chem. Rev.* 73, 141-161 (1973), and J. Chrysochoos, J. Ovadia, L. I. Grossweiner, Pulse radiolysis of aqueous eosin. *J. Phys. Chem.* 71, 1629-1636 (1967), each of which is incorporated by reference in its entirety). The electrostatically corrected standard free energy change $\Delta G°'_{ET}$ is estimated to be −13.8--9.2 kcal/mol using Marcus Theory (FIGS. 3A and 13). Detection of superoxide is difficult, but it typically reduces to hydrogen peroxide in water. See J. E. Natera, W. A. Massad, F. Amat-Guerri, N. A. Garcia, Elementary processes in the eosin-sensitized photooxidation of 3,3'-diaminobenzidine for correlative fluorescence and electron microscopy. "*Journal of Photochemistry & Photobiology, A: Chemistry.*" 220, 25-30 (2011), which is incorporated by reference in its entirety. Hydrogen abstraction from NVP is faster than hydrogen abstraction from TEOA, but Eosin Y regeneration by ground-state electron transfer from $EY.^{3-}$ to $O_2$ appears to be faster than full reduction in presence of both TEOA and NVP (FIG. 14).

Formation of visible-light-absorbing metastable intermediates, like $EY.^{3-}$, from photoredox reactions has been known for decades (see V. Kasche, L. Lindqvist, Transient species in the photochemistry of eosin. *Photochem Photobiol.* 4, 923-933 (1965), S. G. Cohen, A. Parola, G. H. Parsons Jr, Photoreduction by amines. *Chem. Rev.* 73, 141-161 (1973), and J. Chrysochoos, J. Ovadia, L. I. Grossweiner, Pulse radiolysis of aqueous eosin. *J. Phys. Chem.* 71, 1629-1636 (1967), each of which is incorporated by reference in its entirety), but their excitation into photoredox-active states has never been considered. Kimura et al. observed that visible-light irradiation of $EY.^{3-}$ induces debromination in deoxygenated basic methanolic solutions via a hypothesized electron transfer to ground-state Eosin Y (see K. Kimura, T. Miwa, M. Imamura, The radiolysis and photolysis of methanolic solutions of eosin. I. The γ-radiolysis of neutral and alkaline solutions. *Bull. Chem. Soc. Jpn.* 43, 1329-1336 (1970), K. Kimura, T. Miwa, M. Imamura, The radiolysis and photolysis of methanolic solutions of eosin. II. The photo-debromination of eosin in an alkaline solution. *Bull. Chem. Soc. Jpn.* 43, 1337-1342 (1970), and K. Kimura, T. Miwa, M. Imamura, Photochemical debromination of eosin in basic methanolic solution. *Chem. Commun. (London)*, 1619-3 (1968), each of which is incorporated by reference in its entirety). However, the implications and potential of turning these intermediates into photoredox-active species were overlooked. This motivated us to explore the possibility of accelerating the ground-state electron transfer from $EY.^{3-}$ to $O_2$ by photo-activating $EY.^{3-}$. A photoredox-active excited state intermediate ($EY.^{3-}*$) is expected to have a higher ionization potential than its ground state, thus making electron transfer more thermodynamically feasible. Moreover, the standard free energy change for photoinduced electron transfer ($\Delta G°'_{PET}$) will be lower than $\Delta G_{ET}$ by the excess energy of the reacting excited state $E_{0,0}$ (FIGS. 3A and 7), as classically conveyed by the semi-empirical Rehm-Weller equation. While no information is available on the excited states of photoredox intermediates (e.g. $EY.^{3-}$), the rate of photoinduced electron transfer can surely be expected to be faster than the rate of the ground-state electron transfer from $EY.^{3-}$ to $O_2$ (FIG. 1—Step 8). In turn, photoexcitation of $EY.^{3-}$ must accelerate regeneration by $O_2$, shift the $EY.^{3-}/EY-H.^{2-}$ acid-base equilibrium towards $EY.^{3-}$, and reduce photocatalyst "death" (FIG. 3A).

Figure 5:
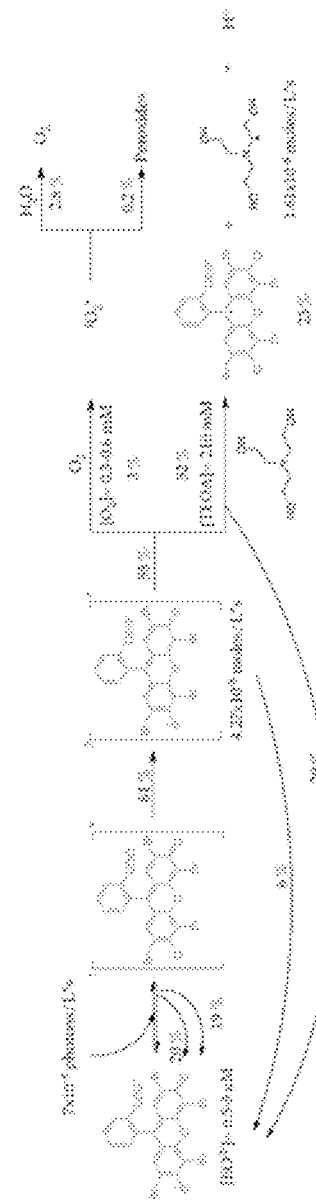
FIG. 5 shows photochemical and photophysical pathways competing with the photoinduced electron transfer from TEOA to Eosin Y in basic (pH 9-10) aqueous solutions.
Figure 10:
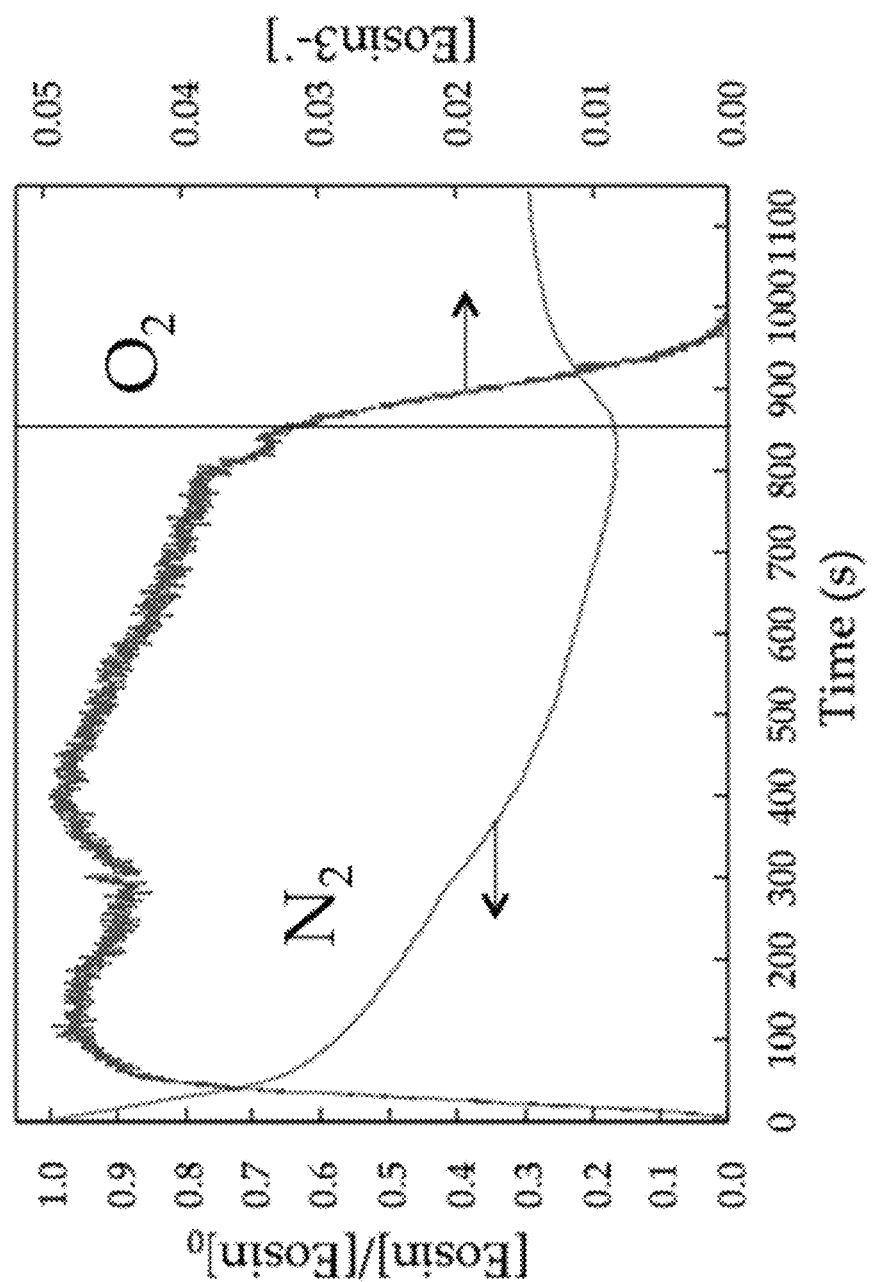
FIG. 10 shows steady-state spectroscopy of the photoreduction of Eosin Y by TEOA driven by green light in deoxygenated aqueous solutions, and the effect of re-oxygenation on the concentration of Eosin Y and EY.$^{3-}$.
Figure 19A:
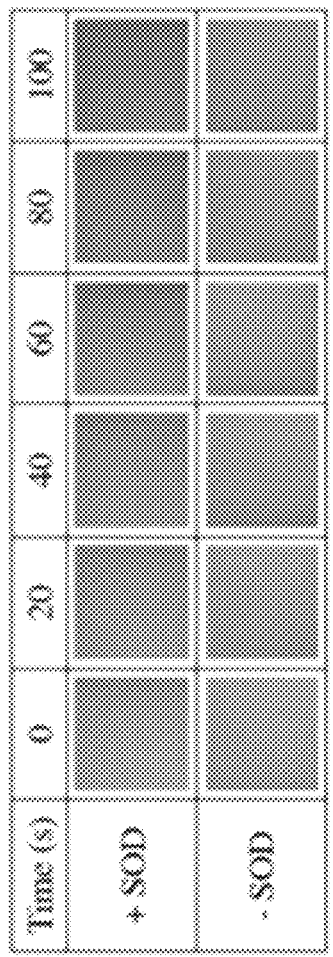
FIGS. 19A-19B show the production of superoxide as support of the regeneration of Eosin Y by reaction of the metastable radical trianion with oxygen.
Figure 19B:
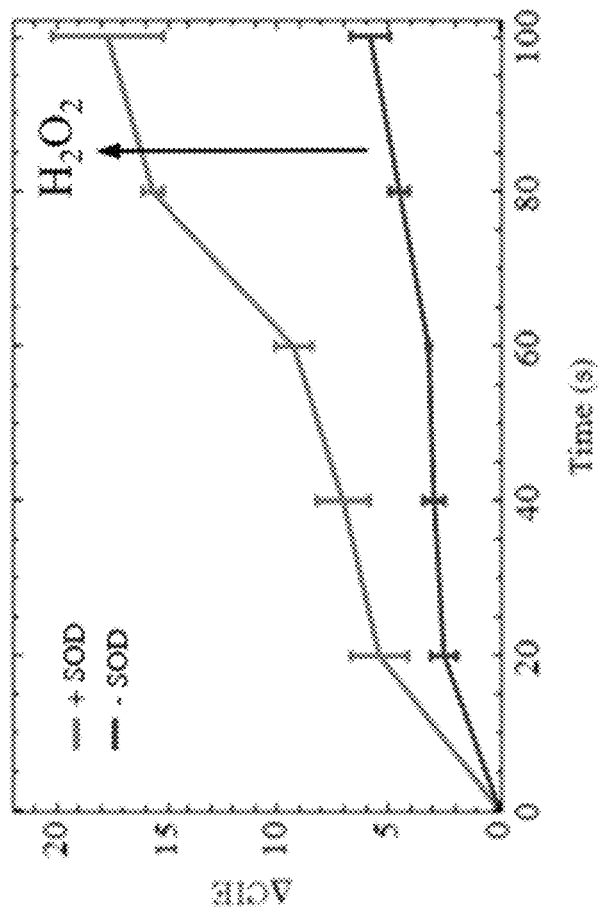

Production of superoxide was shown as evidence of the oxidation of EY.3– by dioxygen. The presence of superoxide was confirmed as support of the ground-state electron transfer from EY.3– to $O_2$. Superoxide is known to readily decay by disproportionation to oxygen and hydrogen peroxide. Superoxide dismutase (SOD) was utilized for the detection of superoxide via a colorimetric peroxidase assay in monomer-free solutions (FIGS. 19A-19B). FIG. 19A shows the effect of the presence of superoxide dismutase (SOD) in hydrogen peroxide detection assay for solutions irradiated for 0-100 seconds with ~500 nm light. The intensity of blue color is proportional to the concentration of hydrogen peroxide. FIG. 19B shows CIELAB color space was used to quantify the differences between samples. ΔCIE values were calculated by subtracting the values for samples that were not irradiated from each irradiation time point. Data points indicate the average of three replicates, and error bars represent standard deviations. Quantification of the colorimetric results clearly shows that superoxide was produced in proportion to irradiation dose, and this intermediate was converted to hydrogen peroxide catalytically by superoxide dismutase. Results clearly show a significant increase in the color associated with the production of hydrogen peroxide when SOD is present (FIGS. 19A and 19B). These observations support the production of superoxide under aerobic irradiation, which most likely results from the ground-state electron transfer of EY.3– to O2 at the present concentrations of oxygen, TEOA, and NVP (FIG. 5). Eosin Y regeneration by ground-state electron transfer from EY.3– to O2 is exergonic (FIGS. 10 and 13). See Cohen S G, Parola A, Parsons G H (1973) Photoreduction by amines. *Chem Rev* 73: 141-161, Hammes-Schiffer S (2009) Theory of proton-Coupled electron transfer in energy conversion processes. *Acc Chem Res* 42: 1881-1889, and Gray H B, Winkler J R (2005) Long-range electron transfer *Proc Natl Acad Sci USA* 102: 3534-3539, each of which is incorporated by reference in its entirety. The electrostatically corrected standard free energy change ΔG°'ET is estimated between −(13.8-9.2 kcal/mol), using Marcus Theory (FIG. 13). A kinetic constant for electron transfer cannot be estimated with the available information, but the kinetic experiments indicate this reaction is at the most two-orders of magnitude from diffusion-controlled.

Figure 3B:
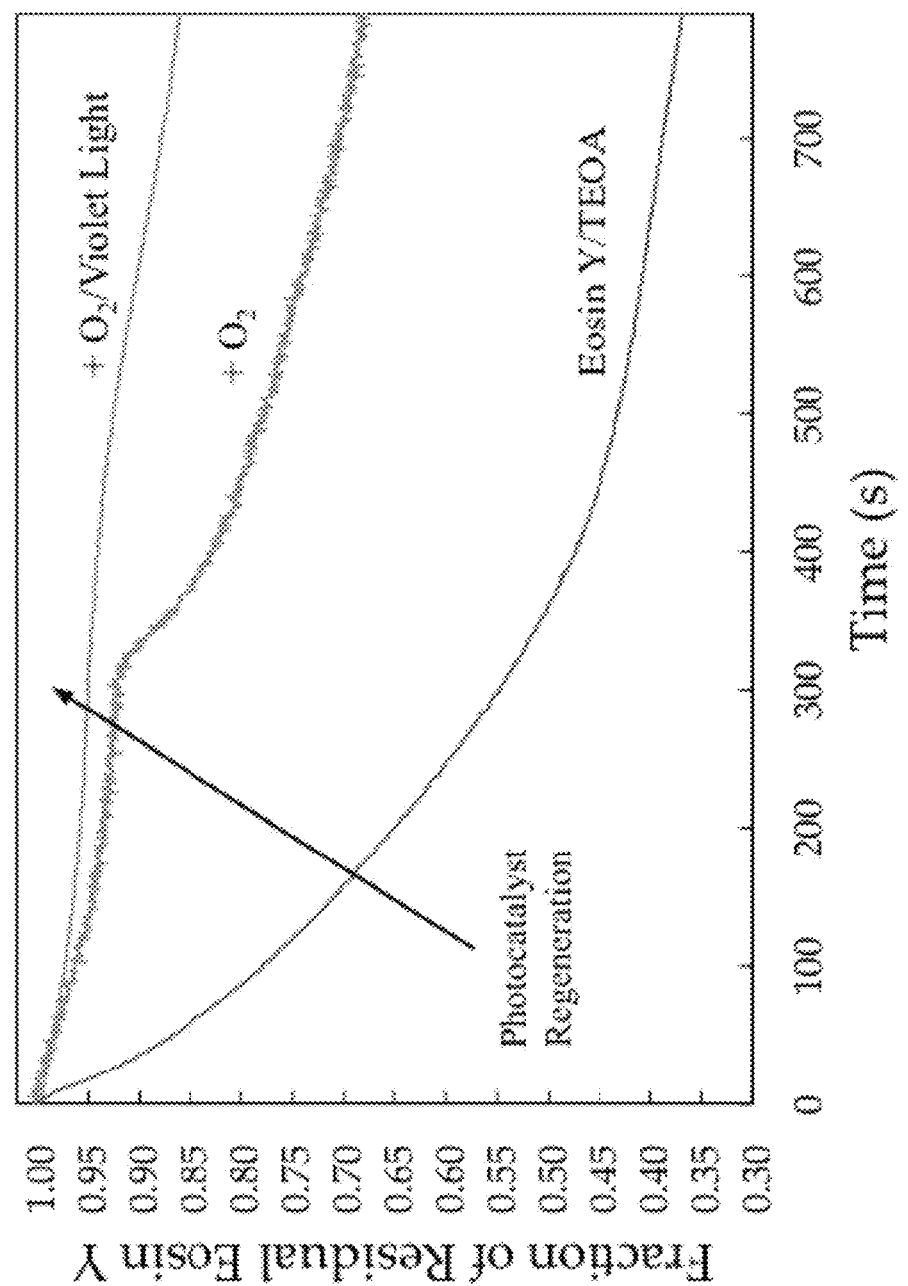

The rate of Eosin Y regeneration is faster when $EY.^{3-}$ absorbs a violet (405 nm) photon in the presence of $O_2$ (FIG. 3B). This is the opposite of what would be expected from absorption of the violet photons by Eosin Y. These initial observations are impressive considering that the irradiance at 405 nm is at least two orders of magnitude weaker (microwatts) than the 500 nm radiation exciting Eosin Y (FIG. 3B). Only 15% Eosin Y was consumed after 800 s of irradiation, which constitutes 20% more regeneration from the photoinduced electron transfer than from the ground-state electron transfer. As expected, photoinduced electron transfer to $O_2$ is more efficient than full reduction by hydrogen abstraction from NVP by the EY-H.² intermediate (FIG. 14). Neither energy transfer to $O_2$ nor hydrogen transfer to peroxy radicals can explain this increase in Eosin Y regeneration under violet light. This light-assisted photocatalyst regeneration is presented as evidence of the proposed mechanism and of its utility to enhance the resilience to $O_2$ inhibition. While green light drives photoreduction of Eosin Y to $EY.^{3-}$, violet light accelerates conversion of $EY.^{3-}$ back to Eosin Y (FIG. 1). When violet and green LED's are used together, the rate of single electron transfer from $EY.^{3-}$ to $O_2$ is accelerated. More $EY^{3.-}$ is converted back into Eosin Y, thus reducing the rate of photocatalyst "death".

As the initial $O_2$ concentration increased upon addition of the hydrogel precursor (PEGDA), exposure to violet light in the presence of oxygen resulted in 100% Eosin Y regeneration during oxygen inhibition, i.e. Eosin Y concentration remained constant (FIGS. 4A and 15) (see K. Kaastrup, A. Aguirre-Soto, C. Wang, C. N. Bowman, J. W. Stansbury, H.

Figure 4B:
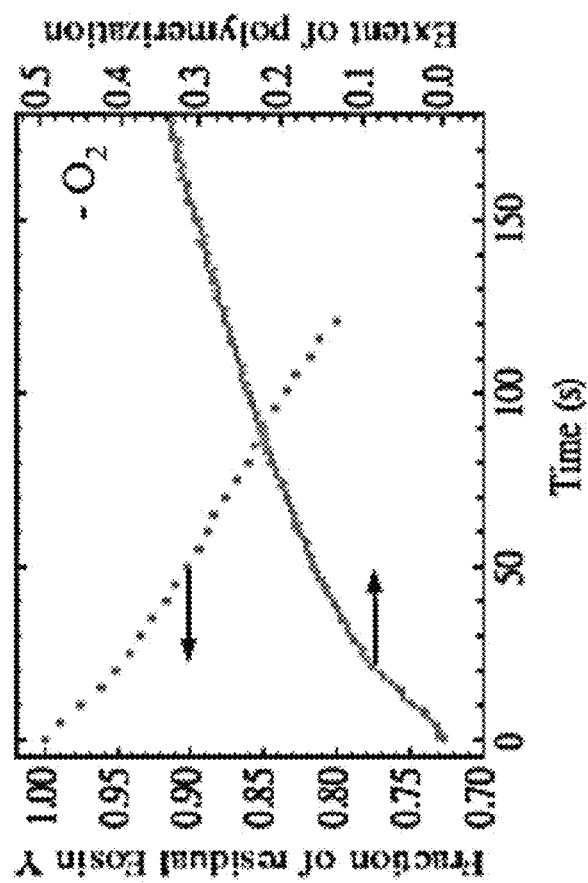
FIGS. 4A-4D show light-assisted photocatalyst regeneration for oxygen-resilient radical polymerization and conserving Eosin Y during oxygen inhibition.
Figure 4A:
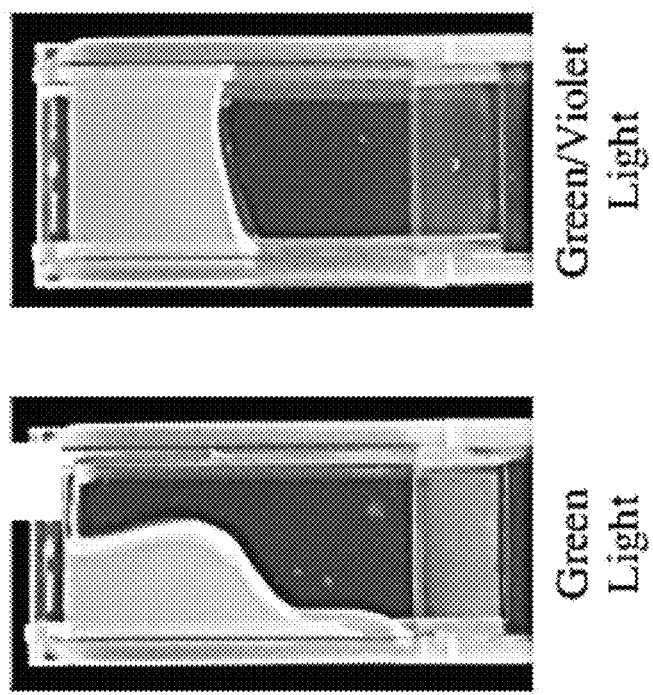
Figure 4C:
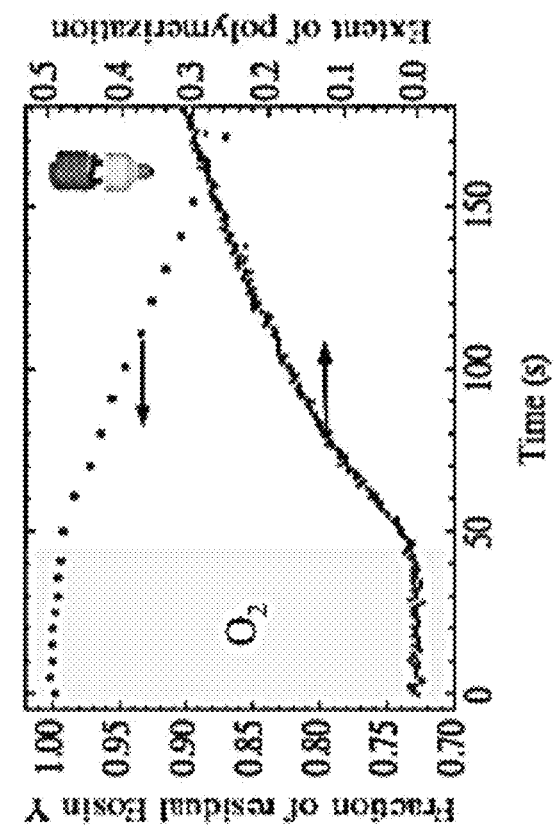
Figure 4D:
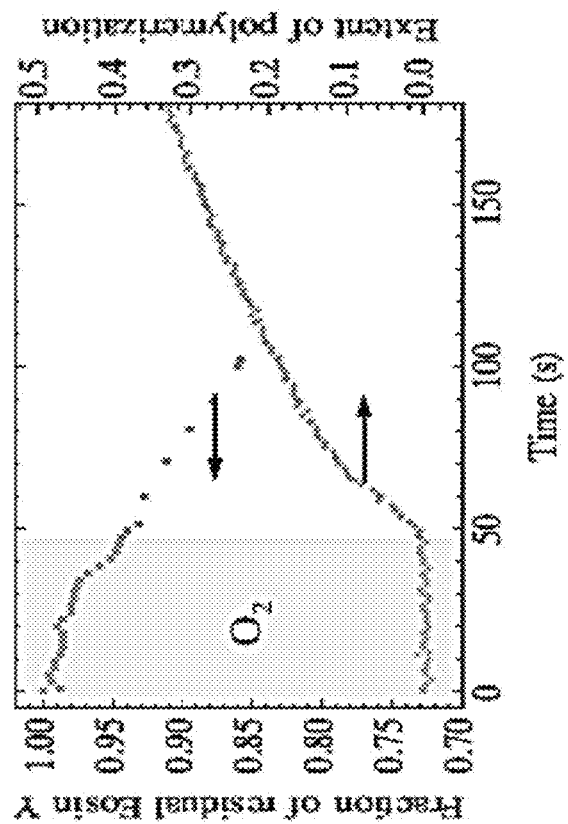
Figure 16:
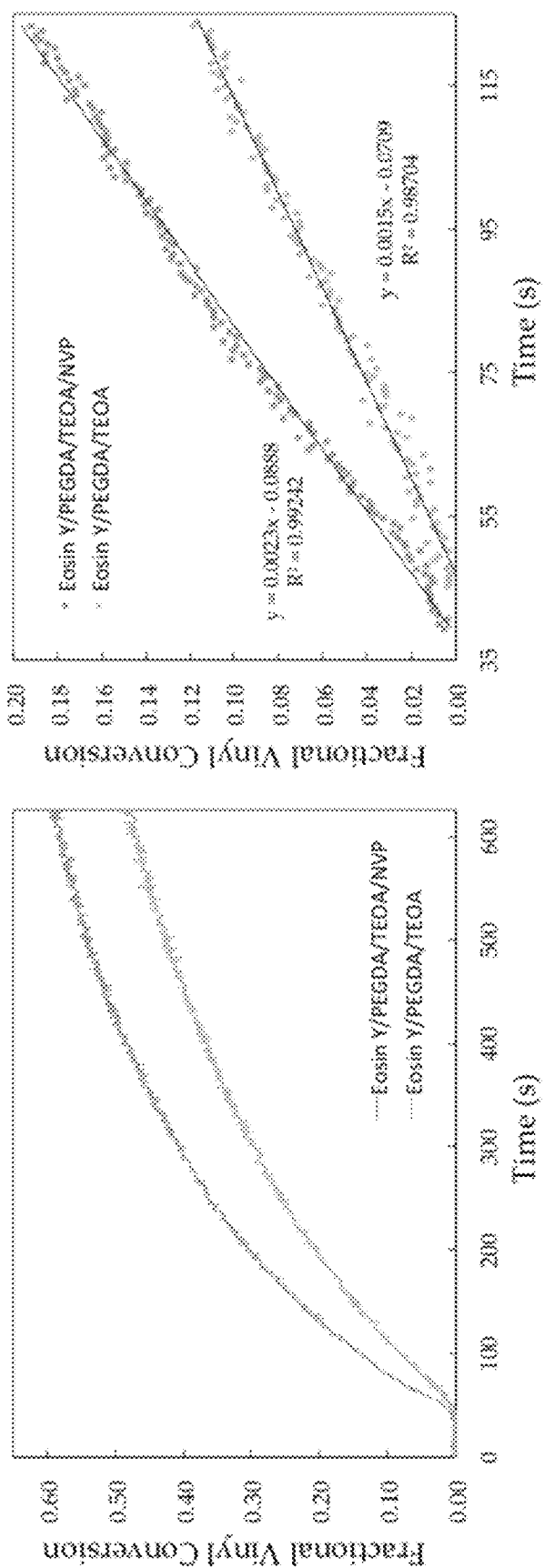
FIG. 16 shows fractional vinyl conversion from steady-state spectroscopy experiments with simultaneous UV-Vis/FT-NIR in the presence and absence of NVP.

D. Sikes, UV-Vis/FT-NIR in situ monitoring of visible-light induced polymerization of PEGDA hydrogels initiated by eosin/triethanolamine/O 2. *Polym. Chem.* 7, 592-602 (2016), which is incorporated by reference in its entirety). In the absence of $O_2$, the rate of Eosin Y consumption and polymerization were the same with or without violet light. The rate of Eosin Y consumption in the oxygen-free experiments was the same as the rate obtained after $O_2$ depletion without violet light. As expected from the mechanism, no polymerization was observed without TEOA and twice the rate of initiation was obtained by addition of NVP to Eosin Y/TEOA solutions (FIG. 16). Exposure to low-intensity violet light in the presence of $O_2$ reduced the inhibition time ($t_{inh}$) from 49 s to 43 s (FIGS. 4B-4D). Higher-intensity violet light only led to a slightly faster (~5 s) gelation threshold irradiation times than green light alone (FIG. 4A). This is consistent with the proposed mechanism, where two initiating radicals are produced for every "dead" Eosin Y, whereas only one initiating radical appears to be produced for every regenerated Eosin Y. Thus, while violet light enhances photocatalyst regeneration, it can lead to slightly slower oxygen consumption by the well-known chain peroxidation process. See, S. C. Ligon, B. Husár, H. Wutzel, R. Holman, R. Liska, Strategies to reduce oxygen inhibition in photoinduced polymerization. *Chem. Rev.* 114, 557-589 (2014), which is incorporated by reference in its entirety. The gelation was confirmed to start earlier with higher violet irradiance, as shown in FIG. 4A. Thus, increasing the resilience to $O_2$ inhibition by excitation of the photoredox intermediate $EY.^{3-}$, as confirmed by a shorter inhibition time and slightly higher initial rate of polymerization. Four replicates were used to calculate average and standard deviation. Violet light alone results in no polymerization. Conservation of 100% of the initial Eosin Y is achieved only with oxygen and violet light, as the regeneration of Eosin Y becomes highly sensitive to the presence of oxygen. that more Eosin Y is available for polymerization after the inhibition period when green (500 nm) and violet (405 nm) light are used as compared to green light alone. Exposure to green (530 nm) and violet (405 nm) LEDs of oxygenated aqueous solutions containing Eosin Y, triethanolamine and N-vinylpyrrolidone results in faster gelation of the PEGDA hydrogels.

Figure 17:
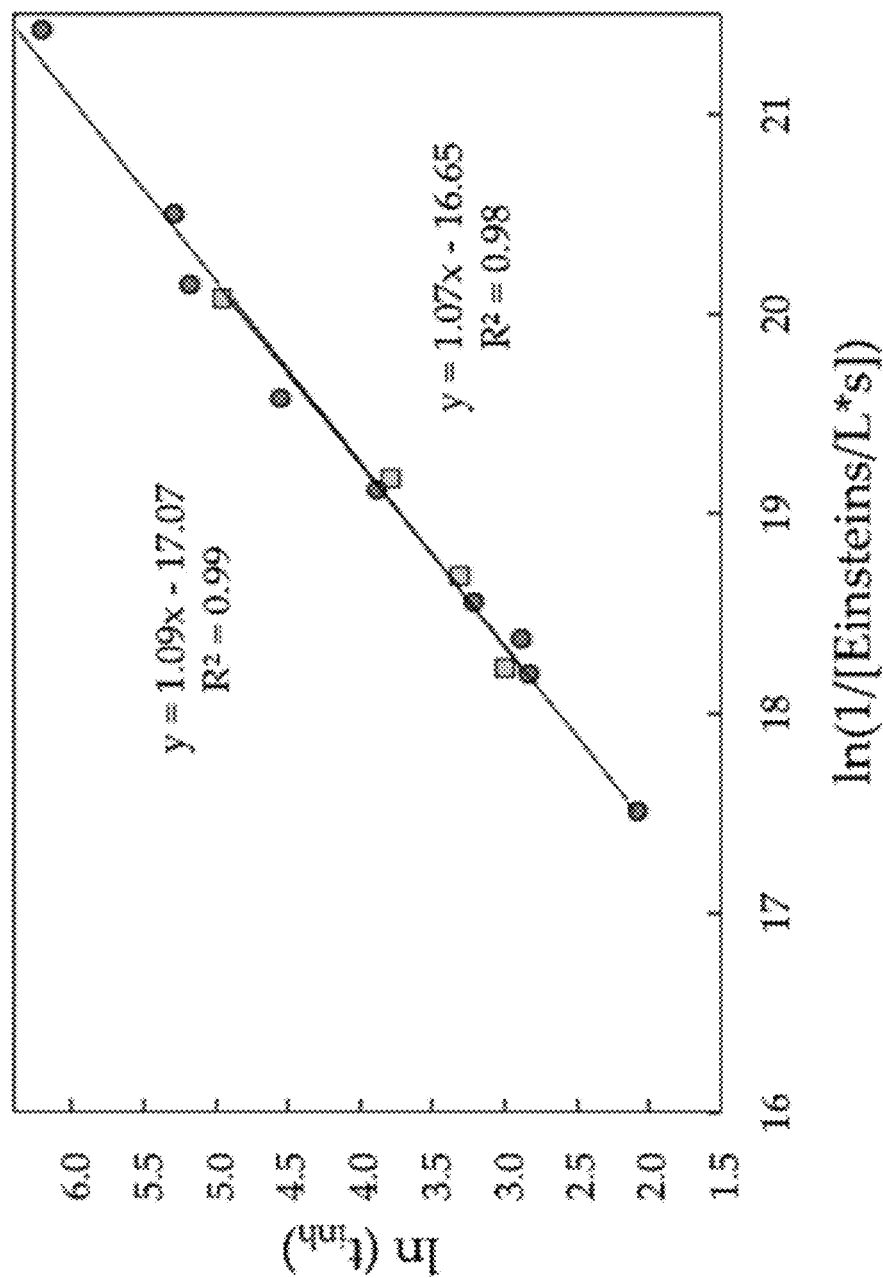
FIG. 17 shows oxygen inhibition time ($t_{inh}$) scales linearly with the rate of photon absorption, determined by the initial Eosin Y concentration and the irradiance of the green LED (500 nm) used in the steady-state spectroscopy experiments.
Figure 18:
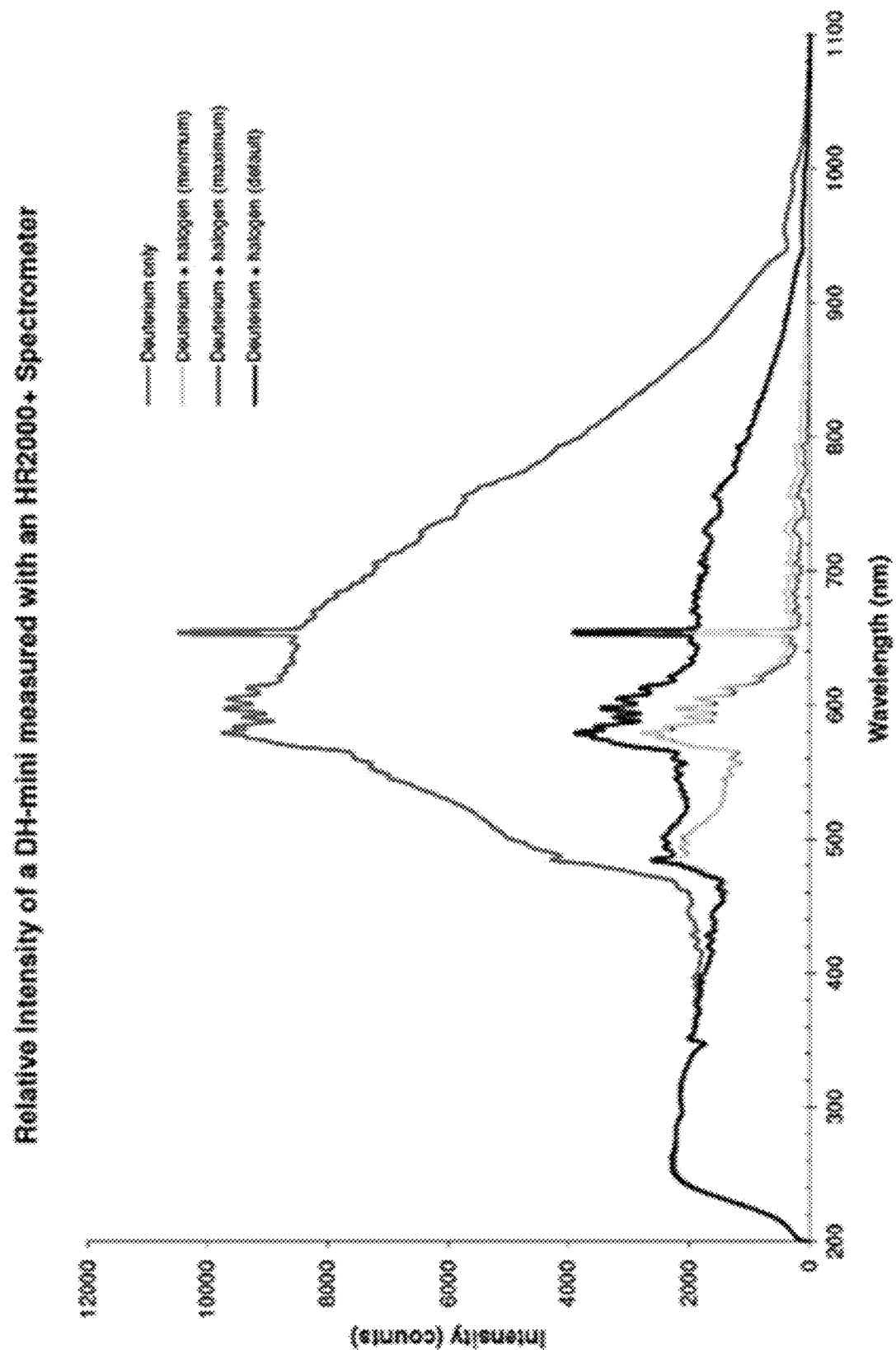
FIG. 18 shows relative intensities of the two lamps used during experiment to excite the intermediates and to monitor de decay of the photocatalyst simultaneously in real-time.

At least hundreds of $O_2$ molecules are consumed per photon absorbed, as obtained from analysis of the rate of photon absorption ($7*10^{-8}$ Einsteins/L*s) and the $O_2$ consumption (FIG. 4A). This indicates that a chain process must be involved in $O_2$ depletion, and that a primary photochemical process alone cannot explain the high resilience to $O_2$ inhibition. The proposed photoredox cycle directly consumes one $O_2$ per photon absorbed (FIG. 1), but radical chain peroxidation helps in consuming excess $O_2$ faster than the rate of oxygen replenishment (FIG. 1—Islet). NVP provides the most labile hydrogens, enhancing $O_2$ depletion via chain peroxidation, as supported by a reduction in $t_{inh}$ upon addition of NVP (FIG. 16). Moreover, $t_{inh}$ scales linearly with Eosin Y concentration and irradiance (FIG. 17). This would be expected of a 1:1 $O_2$ per absorbed photon ratio, i.e. when the rate of radical production approaches the rate of chain peroxidation. Here, however, the rate of photon absorption is limiting by several orders of magnitude as compared to the fast chain peroxidation. See, J. Wong, K. Kaastrup, A. Aguirre-Soto, H. D. Sikes, A quantitative analysis of peroxy-mediated cyclic regeneration of eosin under oxygen-rich photopolymerization conditions. *Polymer.* 69, 169-177 (2015), and J. Wong, H. D. Sikes, The impact of continuous oxygen flux in a thin film photopolymerization reaction with peroxy-mediated regeneration of initiator. *Macromolecular Theory and Simulations.* 25, 229-237 (2016), each of which is incorporated by reference in its entirety. Therefore, $t_{inh}$ scales linearly with intensity even when hundreds of $O_2$ molecules are consumed per photon absorbed.

The concept of light-assisted photocatalyst regeneration was introduced to increase photocatalyst turnover, reduce photocatalyst "death" and aid in overcoming $O_2$ inhibition in organic visible-light driven polymerization and crosslinking reactions. The interest in this mechanism stems from the need to form hydrogels at interfaces for the detection of biomolecular markers for point-of-care medical diagnostics, for which the present formulation has resulted in the best performance. See, L. Kuck, A. Taylor, Photopolymerization as an innovative detection technique for low-density microarrays. *Biotech.* 45, 179-186 (2008), A. K. Badu-Tawiah, S. Lathwal, K. Kaastrup, M. Al-Sayah, D. C. Christodouleas, B. S. Smith, G. M. Whitesides, H. D. Sikes, Polymerization-based signal amplification for paper-based immunoassays. *Lab Chip.* 15, 655-659 (2015), H. D. Sikes, R. Jenison, C. N. Bowman, Antigen detection using polymerization-based amplification. *Lab Chip.* 9, 653-656 (2009), and S. Lathwal, H. D. Sikes, Assessment of colorimetric amplification methods in a paper-based immunoassay for diagnosis of malaria. *Lab Chip.* 16, 1374-1382 (2016), each of which is incorporated by reference in its entirety. Light-assisted photocatalyst regeneration promises improvements in the specificity of polymerization-based signal amplification. However, the applicability of light-assisted photocatalyst regeneration extends beyond medical diagnostics into the development of more sensitive oxygen sensors, lower cost environmentally benign chemical synthesis, precise macromolecular design, higher yields of hydrogen production, 2D and 3D photolithography, and safer photomedical treatments, to name a few. See, D. B. Papkovsky, New oxygen sensors and their application to biosensing. *Sensors and Actuators B: Chemical.* 29, 213-218 (1995), D. M. Schultz, T. P. Yoon, Solar synthesis: Prospects in visible light photocatalysis. *Science.* 343, 1239176-1239176 (2014), J. C. Theriot, C. Lim, H. Yang, M. D. Ryan, C. B. Musgrave, G. M. Miyake, Organocatalyzed atom transfer radical polymerization driven by visible light. *Science.* 352, 1-10 (2016), Q. Li, B. Guo, J. Yu, J. Ran, B. Zhang, H. Yan, J. R. Gong, Highly efficient visible-light-driven photocatalytic hydrogen production of CdS-cluster-decorated graphene nanosheets. *J. Am. Chem. Soc.* 133, 10878-10884 (2011), and Y. Kamegaya, W. M. Farinelli, A. V. Vila Echague, H. Akita, J. Gallagher, T. J. Flotte, R. R. Anderson, R. W. Redmond, I. E. Kochevar, Evaluation of photochemical tissue bonding for closure of skin incisions and excisions. *Lasers Surg. Med.* 37, 264-270 (2005), each of which is incorporated by reference in its entirety. Light-assisted photocatalyst regeneration is expected to be applicable to other families of organic photocatalysts as well, which have been observed to produce visible-light absorbing metastable intermediates. See, S. Dadashi-Silab, S. Doran, Y. Yagci, Photoinduced electron transfer reactions for macromolecular syntheses. *Chem. Rev.* (2016), and S. G. Cohen, A. Parola, G. H. Parsons Jr, Photoreduction by amines. *Chem. Rev.* 73, 141-161 (1973), each of which is incorporated by reference in its entirety. Light-assisted photocatalyst regeneration can be replicated with other laser and LED configurations, and is not restricted to regeneration with oxygen. An oxidant can be added to regenerate the photocatalyst controllably. This concept can allow the use of lower electron affinity oxidants to improve the notoriously problematic thermal instability without compromising the radical production and initiation efficiency.

FIG. 5 shows photochemical and photophysical pathways competing with the photoinduced electron transfer from TEOA to Eosin Y in basic (pH 9-10) aqueous solutions. The excited triplet can accept an electron, donate an electron, or donate its excess energy. However, no oxidants are present with sufficient ionization potential for photo-oxidation of Eosin Y triplet to occur (see FIG. 13 for standard reduction potentials). Energy transfer from $^3\text{EY}^{2-*}$ to $O_2$ is well-known in the absence of reductants, but singlet oxygen has a short lifetime in water to initiate subsequent chemical reactions, and does not participate when a tertiary amine reductant is present. See, M. Montalti, A. Credi, L. Prodi, M. T. Gandolfi, *Handbook of Photochemistry, Third Edition* (CRC Press, 2006), P. Ogilby, C. S. Foote, Chemistry of singlet oxygen. 42. Effect of solvent, solvent isotopic substitution, and temperature on the lifetime of singlet molecular oxygen (1Δg). *J. Am. Chem. Soc.* 105, 3423-3430 (1983), and R. F. Bartholomew, R. S. Davidson, The photosensitised oxidation of amines. Part II. The use of dyes as photosensitisers: evidence that singlet oxygen is not involved. *J. Chem. Soc., C*, 2347-5 (1971), each of which is incorporated by reference in its entirety. From experimentally derived rate constants, the quantum yields of electron and energy transfer are 0.23 and 0.02, respectively. For reference 6701 see the Handbook of Photochemistry. See, M. Montalti, A. Credi, L. Prodi, M. T. Gandolfi, *Handbook of Photochemistry, Third Edition* (CRC Press, 2006), and M. V. Encinas, A. M. Rufs, S. G. Bertolotti, C. M. Previtali, Xanthene dyes/amine as photoinitiators of radical polymerization: A comparative and photochemical study in aqueous medium. *Polymer.* 50, 2762-2767 (2009), each of which is incorporated by reference in its entirety.

Figure 6:
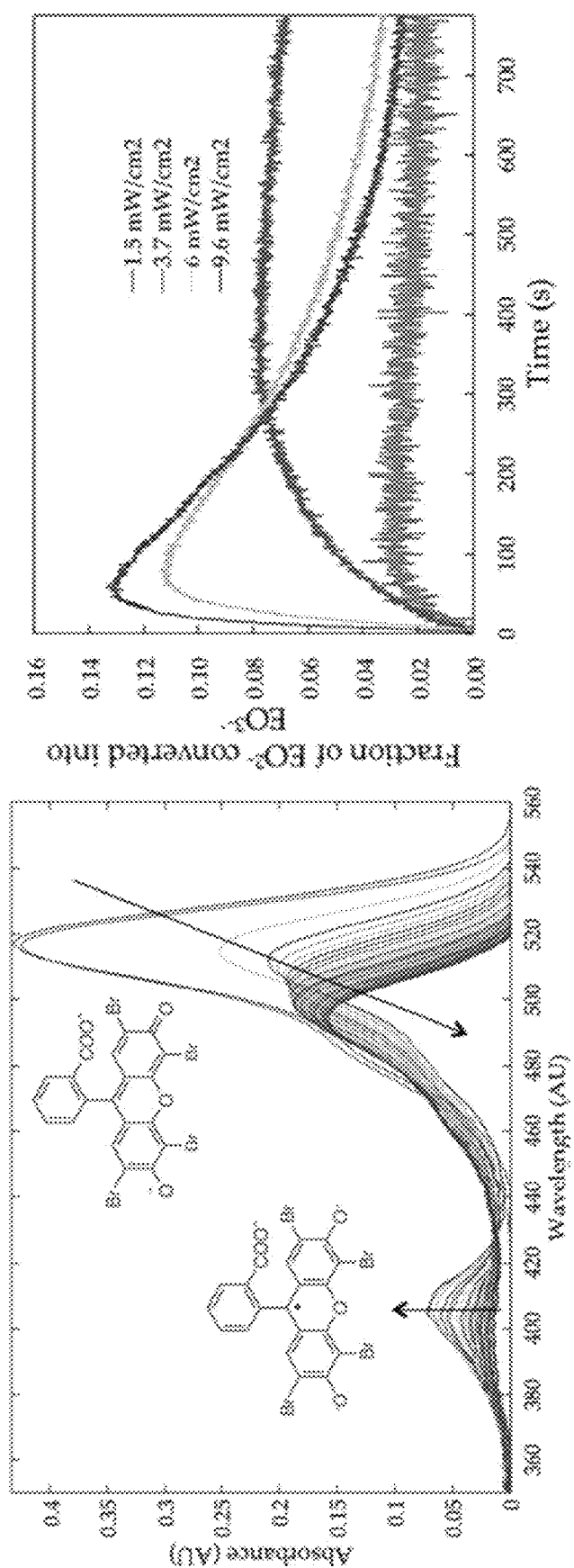
FIG. 6 shows production of the visible-light absorbing metastable radical trianion (EY.$^{3-}$) as a function of irradiance from steady-state experiments in Eosin Y/TEOA aqueous solutions.

FIG. 6 shows production of the visible-light absorbing metastable radical trianion ($\text{EY}^{3-}$) as a function of irradiance from steady-state experiments in Eosin Y/TEOA aqueous solutions. Others have observed the same peak around 406 nm, including under γ-radiation, and unequivocally assigned it to $\text{EY}^{3-}$ by electron paramagnetic resonance spectroscopy. See, K. Kimura, T. Miwa, M. Imamura, The radiolysis and photolysis of methanolic solutions of eosin. I. The γ-radiolysis of neutral and alkaline solutions. *Bull. Chem. Soc. Jpn.* 43, 1329-1336 (1970), K. Kimura, T. Miwa, M. Imamura, The radiolysis and photolysis of methanolic solutions of eosin. II. The photo-debromination of eosin in an alkaline solution. *Bull. Chem. Soc. Jpn.* 43, 1337-1342 (1970), K. Kimura, T. Miwa, M. Imamura, Photochemical debromination of eosin in basic methanolic solution. *Chem. Commun. (London)*, 1619-3 (1968), and K. Kimura, M. Imamura, Studies of the ESR spectra of semiquinone anions of xanthene dyes. Variation in the linewidth of the phloxine semiquinone anion with the temperature and the viscosity in protic solvents *Bull. Chem. Soc. Jpn.* 47, 1358-1362 (1974), each of which is incorporated by reference in its entirety. Its frequency and low extinction coefficient are due to loss of aromaticity when Eosin Y accepts a single electron ($e^-$). The concentration of $\text{EY}^{3-}$ increased with irradiance as $\text{EY}^{3-}$ forms by photoinduced electron transfer from the reductant (TEOA) to the excited triplet $^3\text{EY}^{2-*}$ dianion (FIG. 1—Step 3). From the plot on the right, it is observed that the yield of $\text{EY}^{3-}$ appears to be dependent on the acid/base equilibrium $\text{EY}^{3-}/\text{EY-H}^{2-}$, where the protonation rate balances the $\text{EY}^{3-}$ production rate.

Figure 7:
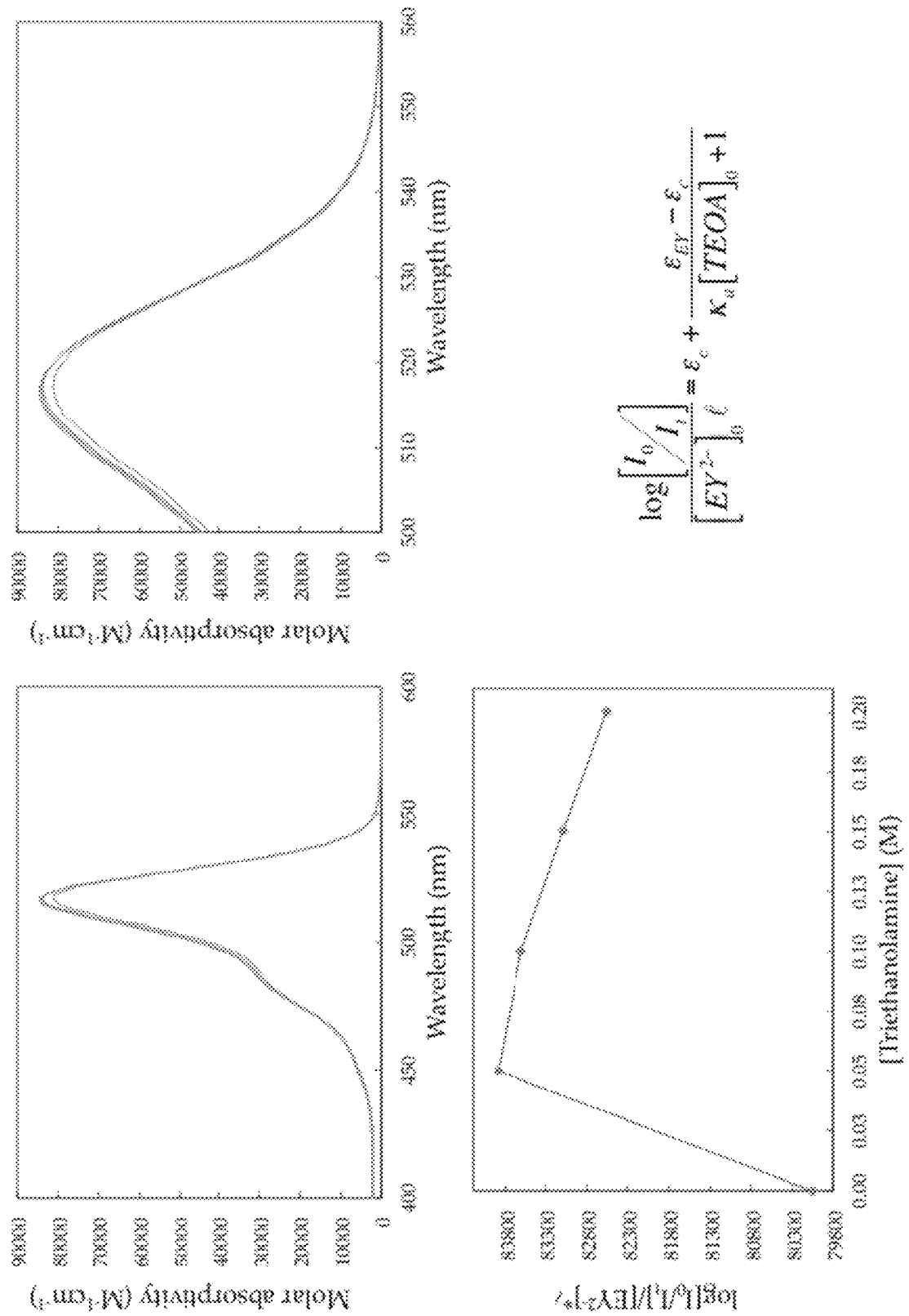
FIG. 7 shows electron-donor-acceptor complex formation between Eosin Y and Triethanolamine (TEOA) in aqueous solutions.

FIG. 7 shows electron-donor-acceptor complex formation between Eosin Y and Triethanolamine (TEOA) in aqueous solutions. An Eosin Y/TEOA (1:1) electron-donor-acceptor complex ($K_a$=90±30 $M^{-1}$) was confirmed from a nonlinear regression using a modified Benesi-Hildebrand equation, as shown in the bottom right. The same result was obtained in the presence of PEGDA with slightly different association constant. Similar weakly bound charge-transfer complexes have been reported for Eosin Y and other xanthene dyes. The charge-transfer complexes appear to be correlated to increases in the rate of electron transfer without concomitantly increasing the rate of back electron transfer. See, D. Kim, A. B. Scranton, J. W. Stansbury, Analysis of association constant for ground-state dye-electron acceptor complex of photoinitiator systems and the association constant effect on the kinetics of visible-light-induced polymerizations. *J. Polym. Sci. A Polym. Chem.* 47, 1429-1439 (2009), which is incorporated by reference in its entirety. The heavy bromine atoms of Eosin Y has been proposed to provide enough complexation for $e^-$ transfer without hindering the dissociation of the solvated radical ion pair. See, D. R. Weinberg, C. J. Gagliardi, J. F. Hull, C. F. Murphy, C. A. Kent, B. C. Westlake, A. Paul, D. H. Ess, D. G. McCafferty, T. J. Meyer, Proton-coupled electron transfer. *Chem. Rev.* 112, 4016-4093 (2012), which is incorporated by reference in its entirety.

Figure 8:
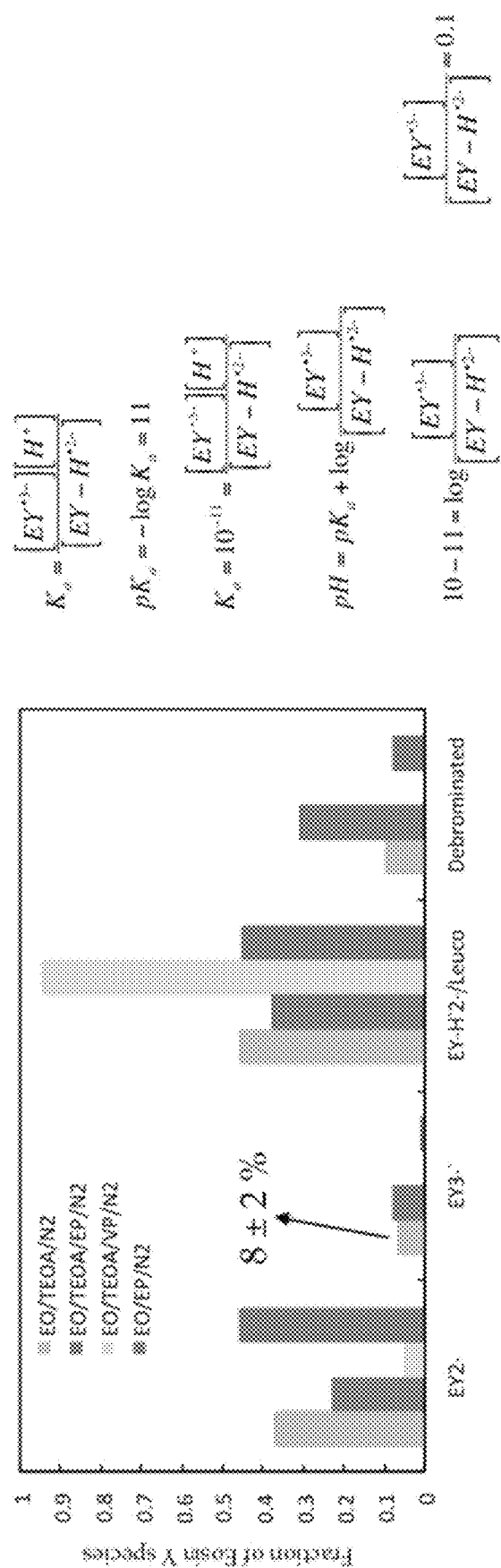
FIG. 8 shows predicted vs calculated yield of the EY.$^{3-}$ intermediate.
Figure 9:
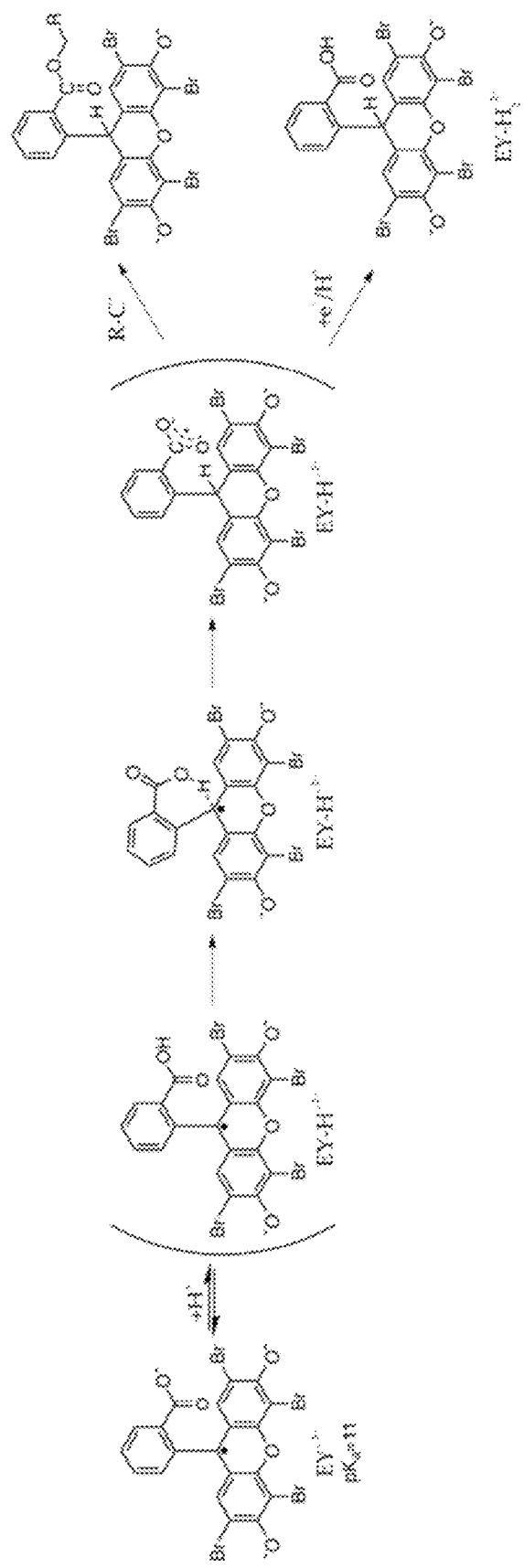
FIG. 9 shows metastable intermediates from the photoreduction of Eosin Y and known reactions of the partially reduced EY-H.$^{2-}$.

FIG. 8 shows predicted vs calculated yield of the $\text{EY}^{3-}$ intermediate. The predicted yield was obtained from the reported acid dissociation constant for $\text{EY}^{3-}$ (pKa 11). On the other hand, the yield calculated by us was obtained from a mass balance of Eosin Y and its photoredox intermediates from the steady-state spectroscopy experiments. A good agreement was found between the 10% $\text{EY}^{3-}$ yield predicted from the acid dissociation constant of $\text{EY-H}^{2-}$, and the yield calculated from the spectroscopic data, 8±2%. $\text{EY}^{3-}$ is known to protonate quickly in acidic aqueous and alcoholic solutions. See, J. Zhang, L. Sun, T. Yoshida, Spectroelectrochemical studies on redox reactions of eosin Y and its polymerization with Zn2+ ions. *Journal of Electroanalytical Chemistry.* 662, 384-395 (2011), which is incorporated by reference in its entirety.

FIG. 9 shows metastable intermediates from the photoreduction of Eosin Y and known reactions of the partially reduced $\text{EY-H}^{2-}$. The formation of a lactone-type structure that can provide some stability has been proposed several times by others, but experimental results are still required to assess the metastability of this specie. Nevertheless, it is expected that $\text{EY-H}^{2-}$ will ultimately abstract a hydrogen atom ($e^-/\text{H}^+$), irreversibly reducing to $\text{EY-H}_2^{2-}$. The results indicate that, in the presence of TEOA, the rate of hydrogen abstraction from TEOA is relatively slow, which can be rationalized as stemming from the delocalization of the oxygen-centered radical in the benzoic acid moiety. This is consistent with the alkylation at the benzoic acid group via radical quenching with carbon-centered radicals used for grafting to polymers and bioconjugation. See, S. Kizilel, V. H. Pérez-Luna, F. Teymour, Photopolymerization of poly (Ethylene Glycol) diacrylate on eosin-functionalized surfaces. *Langmuir.* 20, 8652-8658 (2004), which is incorporated by reference in its entirety. After protonation, intramolecular hydrogen transfer has been theorized, leading to formation of the benzoic acid radical. Then, $\text{EY-H}^{2-}$ can be fully reduced by hydrogen ($e^-/\text{H}^+$) abstraction from NVP (FIG. 1—Step 7). $\text{EY-H}_2^{2-}$ was detected by its peak centered at 308 nm (FIG. 2C), as seen by others via $2e^-/2\text{H}^+$ chemical reduction with sodium borohydride. See, G. Weng, M. A. Mahmoud, M. A. El-Sayed, Nanocatalysts can change the number of electrons involved in oxidation-reduction reaction with the nanocages being the most efficient. *J. Phys. Chem. C.* 116, 24171-24176 (2012), which is incorporated by reference in its entirety.

FIG. 10 shows steady-state spectroscopy of the photoreduction of Eosin Y by TEOA driven by green light in deoxygenated aqueous solutions, and the effect of re-oxygenation on the concentration of Eosin Y and EY.$^{3-}$. Eosin Y is not fully regenerated here because the majority of the Eosin Y has been fully reduced by TEOA from the prolonged irradiation with the green (500 nm) LED at 3 mW/cm$^2$. However, the regeneration of Eosin Y from the smaller fraction of the EY.$^{3-}$ intermediate is quickly regenerated after the deoxygenated sample is opened to oxygen from air.

Figure 11:
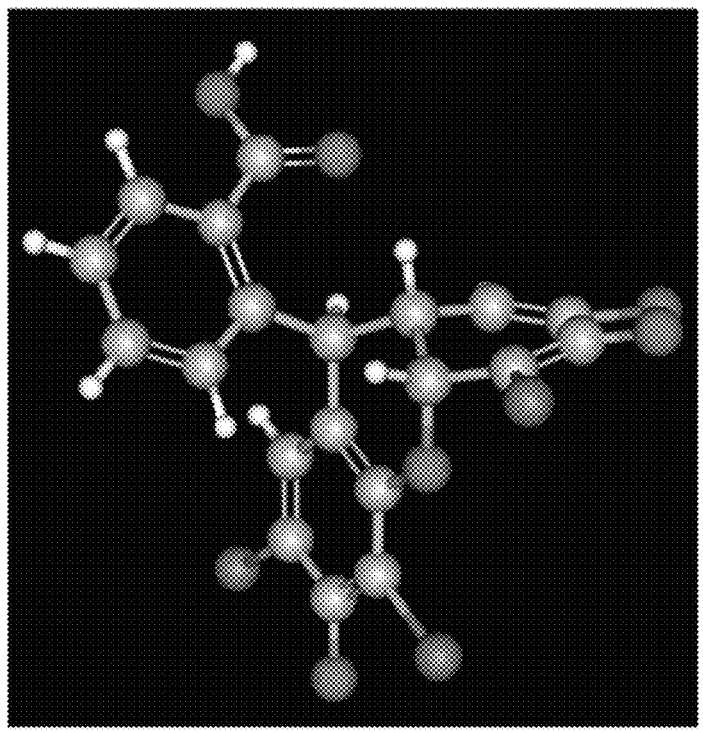
FIG. 11 shows predicted structure for Eosin Y (left) and predicted bent structure of EY-H$_2^{2-}$ from full reduction of Eosin Y (right).
Figure 11:
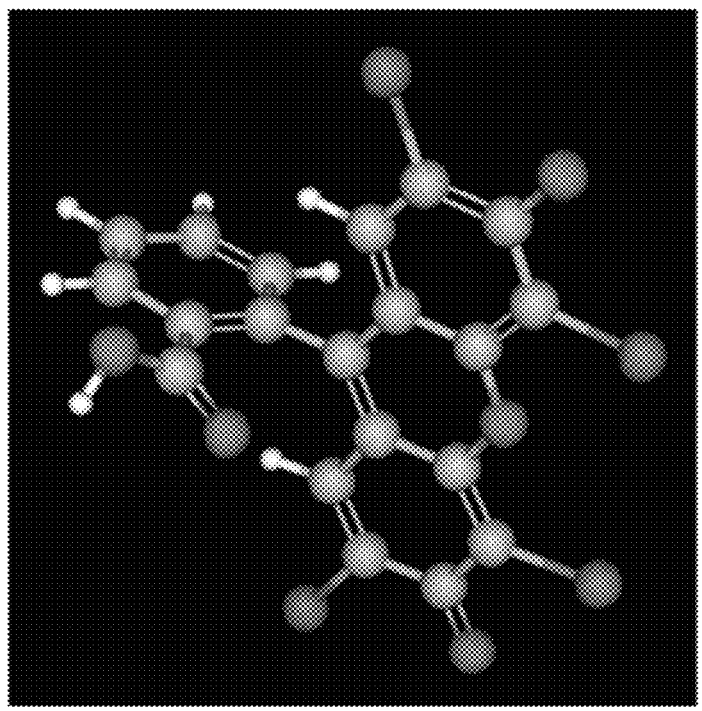

FIG. 11, left, shows predicted structure for Eosin Y and FIG. 11, right, shows predicted bent structure of EY-H$_2$$^{2-}$ from full reduction of Eosin Y. EY-H$_2$$^{2-}$ absorbs only in the UV, as expected from a fully reduced leuco dye, as a result from the loss of aromaticity. See, A. Aguirre-Soto, C.-H. Lim, A. T. Hwang, C. B. Musgrave, J. W. Stansbury, Visible-light organic photocatalysis for latent radical-initiated polymerization via 2e$^-$/H$^+$ transfers: Initiation with parallels to photosynthesis. *J. Am. Chem. Soc.* 136, 7418-7427 (2014), which is incorporated by reference in its entirety. Structures were predicted using Marvin from Chemaxon, as detailed in the Materials and Methods section.

Figure 12:
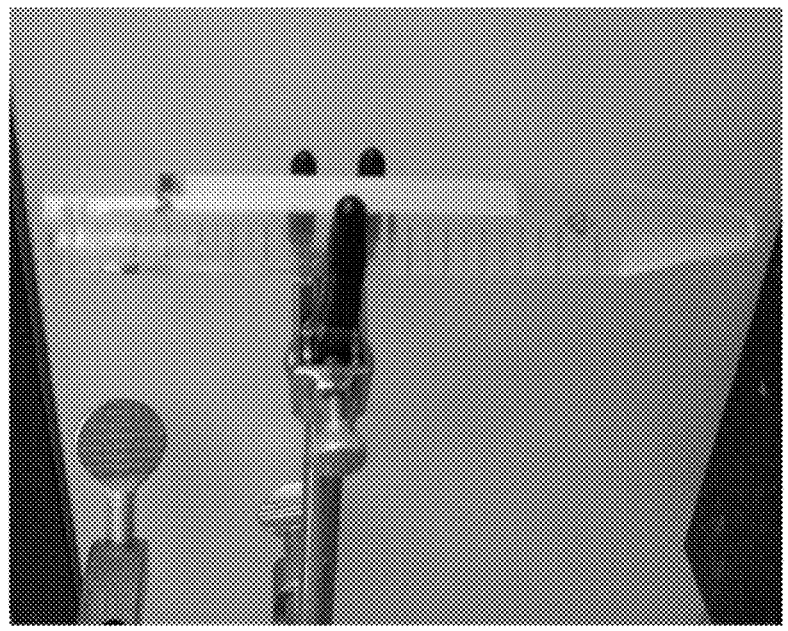
FIG. 12 shows aqueous solution of Eosin Y/TEOA/NVP before and after exposure to a green LED.
Figure 12:
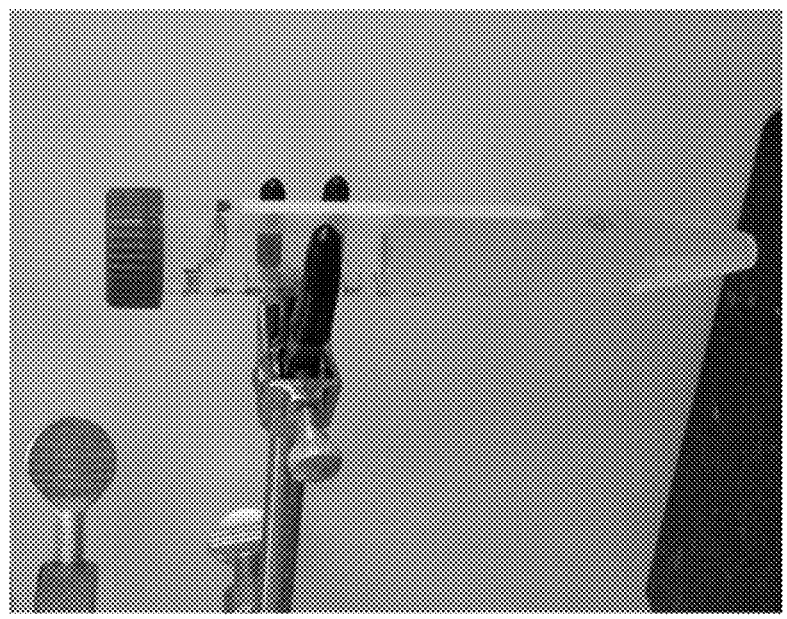

FIG. 12 shows aqueous solution of Eosin Y/TEOA/NVP before and after exposure to a green LED (530 nm) at 35 mW/cm$^2$ where the color does not return for at least weeks after opening the solution to re-oxygenation.

FIG. 13 shows standard free energy change for electron transfer ($\Delta G_{ET}°$) and photoinduced electron transfer ($\Delta G_{PET}°$) and associated kinetic results for consumption of Eosin Y. Electrostatic correction factors were used for the water (−1.4 kcal/mol) and ethylene glycol (−4.48 kcal/mol). Ethylene glycol was used as a reference for the case where reactions take place in PEGDA-rich regions, as detailed in FIG. 15.

Standard free energy change for ground state electron transfer reactions $$\Delta G_{ET}(\text{kcal/mol}) = 23.06\,[E(D^+/D) - E(A/A^-)] + (Z_1 + Z_2 + 1)\frac{e^2 f}{Dr_{12}}$$

Standard free energy change for photoinduced electron transfer reactions $$\Delta G_{ET}(\text{kcal/mol}) =$$
$$23.06\,[E(D^+/D) - E(A/A^-)] - E_{00}^T(\text{kcal/mol}) + (Z_1 + Z_2 + 1)\frac{e^2 f}{Dr_{12}}$$

where E°(D$^+$/D) and E°(A/A$^-$) are standard reduction potentials for the donor (D) and the acceptor (A), Z$_1$ and Z$_2$ are the charges, e denotes the charge of an electron in Coulombs, f is correction for the ionic strength, D is the dielectric of the solvent, r$_{12}$ denotes the radius of the charge transfer complex, and E$^T$$_{00}$ denotes the energy of the excited triplet state. Values for these constants were obtained from the work of Eberson. See, L. Eberson, *Electron Transfer Reactions in Organic Chemistry* (Springer Berlin Heidelberg, Berlin, Heidelberg, 1987), vol. 25 of *Reactivity and Structure Concepts in Organic Chemistry*, and L. EBERSON, S. S. Shaik, Electron-transfer reactions of radical anions: Do they follow outer- or inner-sphere mechanisms? *J. Am. Chem. Soc.* 112, 4484-4489 (1990), each of which is incorporated by reference in its entirety.

FIG. 14 shows steady-stated spectroscopy of the photoreduction of Eosin Y by TEOA in the presence of N-vinylpyrrolidone (NVP) with and without oxygen and exposed to both violet (405 nm) and green (500 nm) light. The electron transfer from EY.$^{3-}$ to O$_2$ is faster than the full reduction of EY-H.2− by NVP as observed from the conservation of >90% the initial Eosin Y concentration during the oxygen depletion region. By ~300 s of irradiation the Eosin Y concentration is less than 10% the initial concentration in the deoxygenated solutions, but >90% in oxygenated solutions. This result further supports the metastability of the EY.$^{3-}$/EY-H.$^{2-}$ intermediates.

Figure 15:
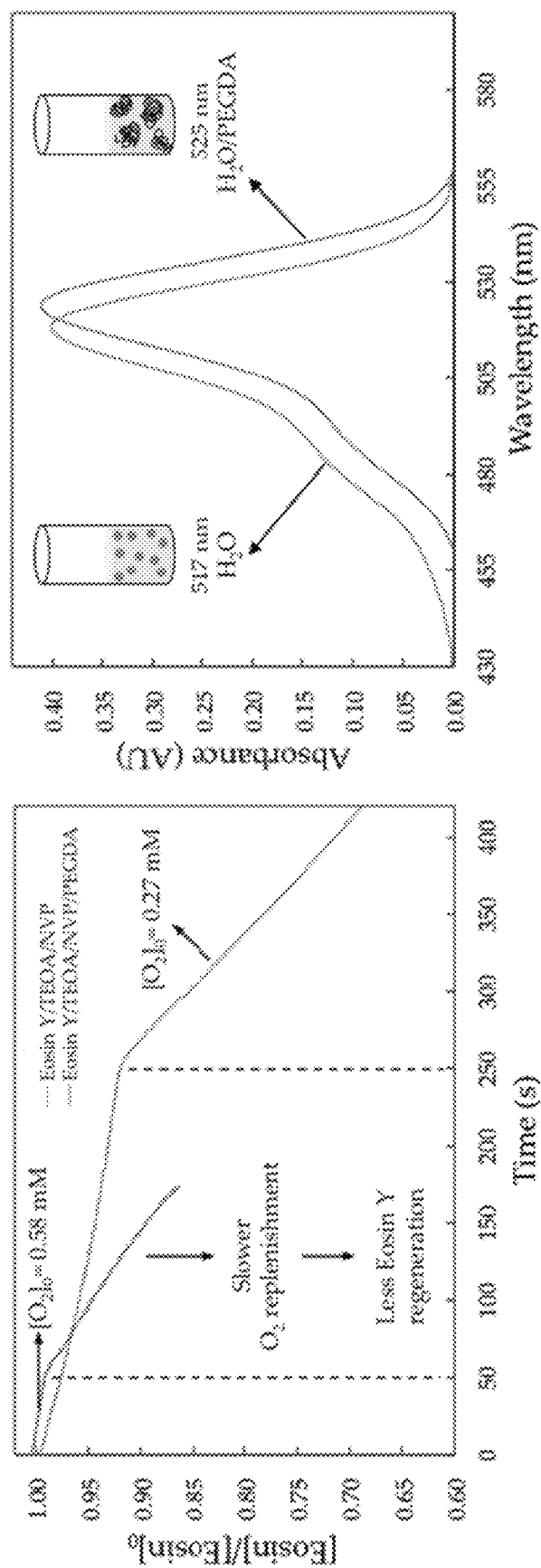
FIG. 15 shows that addition of polyethylene glycol diacrylate (PEGDA) increases initial $O_2$ concentration, but reduces rate of oxygen replenishment after $O_2$ depletion (left). Electronic spectra show that Eosin Y concentrates in the hydrophobic PEGDA-rich micellar-type domains (right).

FIG. 15, left, shows addition of polyethylene glycol diacrylate (PEGDA) increases initial O$_2$ concentration, but reduces rate of oxygen replenishment after O$_2$ depletion. Eosin Y concentration is held almost constant for the initial ~45 s of irradiation. After O$_2$ is consumed, the rate of Eosin Y reduction is faster than the rate in plain water. FIG. 15, right, shows electronic spectra show that Eosin Y concentrates in the hydrophobic PEGDA-rich micellar-type domains. The local Eosin Y concentration is higher in these carbon-rich regions. During the PEGDA crosslinking process, oxygen replenishment into the Eosin Y rich hydrophobic domains is hindered as compared to that in plain water. Thus, Eosin Y is consumed more rapidly after O$_2$ depletion if PEGDA is present. The time to deplete O$_2$ decreased from 250 s in plain water to 50 s with PEGDA, as extracted from the inflections in the rates of Eosin Y consumption. This can be attributed to a lower O$_2$ diffusion when a hydrogel is formed and/or an increase in the local concentration of Eosin Y. It was confirmed that hydrophobic Eosin Y concentrates in the carbon-rich PEGDA micellar-type domains (see, K. Kaastrup, A. Aguirre-Soto, C. Wang, C. N. Bowman, J. W. Stansbury, H. D. Sikes, UV-Vis/FT-NIR in situ monitoring of visible-light induced polymerization of PEGDA hydrogels initiated by eosin/triethanolamine/O 2. *Polym. Chem.* 7, 592-602 (2016), which is incorporated by reference in its entirety), from the shift in its absorbance from 517 nm to 525 nm (as in ethanol), shown in the right. This is analogous to the well-documented nucleation of Eosin Y and other organic dyes around surfactants and proteins (69, 70). See, M. J. Simpson, H. Poblete, M. Griffith, E. I. Alarcon, J. C. Scaiano, Impact of dye-protein interaction and silver nanoparticles on rose bengal photophysical behavior and protein photocrosslinking. *Photochem Photobiol.* 89, 1433-1441 (2013), and N. R. Jana, Z. L. Wang, T. Pal, Redox catalytic properties of palladium nanoparticles: Surfactant and electron donor-acceptor effects. *Langmuir.* 16, 2457-2463 (2000), each of which is incorporated by reference in its entirety. After O$_2$ depletion, the rate of Eosin Y consumption decreased more dramatically in the presence of PEGDA. These observations suggest that aggregation of Eosin Y in the PEGDA-rich regions accelerates O$_2$ depletion, and then Eosin Y is consumed more quickly in the presence of PEGDA because of a lower rate of O$_2$ replenishment.

FIG. 16 shows fractional vinyl conversion from steady-state spectroscopy experiments with simultaneous UV-Vis/FT-NIR in the presence and absence of NVP. The inhibition time (t$_{inh}$) in the presence of NVP is ~36 s, where t$_{inh}$≈50 s in the absence of NVP. From the slopes of the vinyl fractional conversion results between 0 and 20% conversion, the initial rate of polymerization R$_{p0}$ is extracted in order to analyze the relative rates of initiation (R$_i$) from the expected scaling R$_{p0}$=C*R$_i$$^\alpha$, where α=½. This analysis shows that twice the amount of carbon-centered (initiating) radicals are produced in the presence of NVP, as predicted by the mechanism, i.e. as second initiating radical is formed when EY-H.$^{2-}$ abstracts a hydrogen from NVP when oxygen is no longer present for Eosin Y regeneration to occur.

From the experiments with oxygenated solutions, the initial rate of polymerization was extracted after the inhibition period, i.e. oxygen has been depleted almost completely $$\frac{R'_{po}}{R_{p0}} = \frac{0.0023}{0.0015} = 1.5$$

$$\frac{R'_i}{R_i} = \left(\frac{R'_{p0}}{R_{p0}}\right)^2 = (1.5)^2 = 2.3$$

For the experiments in deoxygenated solutions, no inhibition time was observed and the initial rates of polymerization were those obtained immediately after the start of irradiation $$\frac{R'_i}{R_i} = \left(\frac{R'_{p0}}{R_{p0}}\right)^2 = (1.4)^2 = 2$$

where $R_i'$ stands for the rate obtained in the presence of NVP and $R_i$ in the absence of NVP, as for the rates of polymerization $R_{p0}$.

FIG. 17 shows oxygen inhibition time ($t_{inh}$) scales linearly with the rate of photon absorption, determined by the initial Eosin Y concentration and the irradiance of the green LED (500 nm) used in the steady-state spectroscopy experiments. Green dots corresponds to experiments without the violet (405 nm) emission and blue dots correspond to experiments where the violet photons were present. Linear scaling corresponds to a primary photochemical process being the rate-limiting step in the oxygen consumption process. However, the time predicted to consume the initial oxygen concentration by a primary photochemical process where one oxygen molecules is consumed for every absorbed photon is ~6,000 s. In contrast, the time to consumed initial oxygen was observed to be ~50 s. This strongly suggests that chain peroxidation is needed for the oxygen consumption, but that radical production is rate limiting. It was confirmed that the rate of TEOA. production is orders of magnitude smaller than the estimation for the rate of oxygen consumption by chain peroxidation processes. In chain peroxidation, radicals are quenched by $O_2$ to form peroxy radicals, non-reactive towards polymerization. These peroxy radicals efficiently abstract labile hydrogens from TEOA and NVP, creating new initiating carbon-centered radicals in the process. Chain peroxidation is well documented to consume tens of $O_2$ molecules per radical when an alkyl amine is added to Type I UV-photocleaving radical initiators. See, S. C. Ligon, B. Husár, H. Wutzel, R. Holman, R. Liska, Strategies to reduce oxygen inhibition in photoinduced polymerization. *Chem. Rev.* 114, 557-589 (2014), which is incorporated by reference in its entirety.

EXAMPLES

Materials

Poly(ethylene glycol) diacrylate (average $M_n$ 575), triethanolamine (TEOA), 1-vinyl-2-pyrrolidone (NVP), ethyl pyrrolidones (EP), and 2',4',5',7'-tetrabromofluorescein disodium salt (Eosin Y) were purchased from Sigma Aldrich. Distilled water was used.

Preparation of Monomer Solutions

Monomer solutions were prepared containing combinations of 420 mM PEGDA, 35 mM NVP, 210 mM TEOA, and 5 µM Eosin Y in DI water (equivalent to 21.6% PEGDA, 2.8% TEOA, 0.4% NVP, 75.2% water by volume). Concentrations of TEOA and NVP were decreased to 21 mM and to 7 mM, respectively, for the detection of leuco Eosin Y (EY-H$_2^{2-}$) in order to observe the variations in the UV bands of Eosin Y during irradiation. While sub-micromolar concentrations of Eosin Y have been used, micromolar concentrations provide better UV-Vis signal for the kinetic experiments. In the case of the purged samples, argon or nitrogen gas was bubbled through the solution for 5 minutes prior to transfer to the cuvettes for polymerization. All experiments were replicated under nitrogen or argon flow (~8 psi) to test the effect of $O_2$ on the reactions. The reaction chamber was de-oxygenated for ~10 min before the start of irradiation. An average of four replicates were performed for every set of conditions.

Coupled UV-Vis and FT-NIR Monitoring Set-Up

Dual pathlength (10×2 mm) PMMA cuvettes (UVette, Eppendorf, Hauppauge, N.Y.) with transmission in the 220-1600 nm range were used inside a modified UVette adapter (Eppendorf, Hauppauge, N.Y.) with custom optical apertures. The 10 mm pathlength was used for UV-Vis probing based on the molar absorptivities of eosin and the vinyl groups, while the 2 mm pathlength was used for NIR probing, i.e. to allow detection of the low vinyl group concentration from the background associated with the broad —OH bands. The sample volume was 50 µL, which results in sample dimensions of 2 mm×10 mm×2.5 mm, where the latter is the thickness in the direction of the excitation light from the LED. At the initial eosin concentrations used, the 2.5 mm depth ensures operation within the thin-film approximation. Cuvettes were placed inside a CUV-ALL-UV 4-Way Cuvette Holder (Ocean Optics, Dunedin, Fla.) with SMA connectors for fiber integration. Fiber optic cables were connected perpendicularly for UV-Vis and FT-NIR analysis at the same z-plane of ~1.25 mm (half the depth of the sample).

A fiber optic coupled UV-Vis spectrophotometer (USB4000-FL Miniature Fiber Optic Spectrometer, Ocean Optics, Dunedin, Fla.) was used to monitor absorbance within the 350-1000 nm range. A UV-Vis-NIR light source was used to emit the probing beam (DH-Mini, Ocean Optics, Dunedin, Fla.) which contains two bulbs: a deuterium and a halogen bulb. The capability of utilizing these light sources independently allowed us to eliminate the violet light from the probing beam in the kinetic experiments. The UV-Vis probing light was fed into the cuvette holder via a 600 µm solarization resistant fiber optic cable (QP-600-1-SR, Ocean Optics, Dunedin, Fla.), and a 50 µm receiving fiber optic cable (P50-1-Vis-NIR, Ocean Optics, Dunedin, Fla.) was connected to the UV-Vis spectrometer. The collimating lens in the cuvette holder and the ≤1 mm diameter pinhole limit the set of incidence angles of the UV-Vis probing beam in this set-up. The acquisition time for the UV-Vis spectrometer was set to ~0.5 s (50 ms integration time, 10 scans to average) and a boxcar width of 4 was used. A (background) reference spectrum was collected prior to every experiment. Eosin-free solutions of PEGDA, NVP, TEA or combinations thereof showed no absorption in the visible region, but NVP and TEOA absorb strongly in the ultraviolet. Only the water peaks overlap slightly with the R—C=C—H NIR band.

The UV-Vis probing light was adjusted to the same initial threshold intensity (~5,000 photon counts) before every experiment, as recommended by the manufacturer of the spectrophotometer. The UV-Vis probing beams in the span of hours triggered no reaction.

Simultaneous tracking of Eosin Y (517 nm) and EY.$^{3-}$ (406 nm) was achieved by recording light absorption spectra in the 380-700 nm range, as previously described (56, 57). See K. Kaastrup, L. Chan, H. D. Sikes, Impact of dissociation constant on the detection sensitivity of polymerization-based signal amplification reactions. *Anal. Chem.* 85, 8055-8060 (2013), and A. Aguirre-Soto, A. T. Hwang, D. Glugla, J. W. Wydra, R. R. McLeod, C. N. Bowman, J. W. Stansbury, Coupled UV-Vis/FT-NIR spectroscopy for kinetic analysis of multiple reaction steps in polymerizations. *Macromolecules.* 48, 6781-6790 (2015), each of which is incorporated by reference in its entirety. Emission spectra of the deuterium and tungsten/halogen bulbs in the UV-Vis light source used for the steady-state spectroscopy experiments where the tungsten/halogen bulb has no emission below 420 nm, as detected by the spectrophotometer. The effect of eliminating the violet emission was analyzed from the probing beam in the spectroscopic set-up.

A fiber optic coupled FT-NIR spectrometer (Nicolet Magna—IR Series II, Thermo Scientific, West Palm Beach, Fla.) was used to track the vinyl group concentration. FT-NIR spectra were collected with a resolution of 8, a gain of 1, and an optical aperture of 10 with 4 scans to average for every time point. Acquisition time for the FT-NIR was between 0.5 and 3 s. Two 1000 μm fibers were used to feed the NIR probing light from the spectrometer to the sample, and from the sample back into the InGaAs detector. The FT-NIR spectrometer has a built-in white lamp as probing light source. No reaction was observed in the negative controls from exposure to the FT-NIR probing or reference beams.

A high-power fiber coupled multi-wavelength light-emitting diode (LED) light source including a green 500 nm LED (FC8-LED, Prizmatix, Southfield, Mich.) was used to excite eosin and initiate the polymerization from above the sample. Irradiance (power density) was controlled with a built-in potentiometer and measured with a radiometer (6253, International Light Technologies, Peabody, Mass.) within the 400-700 nm range. The fiber optic cable was connected to a collimating (focusing) lens. A 3D printed cap was placed on top of the cuvette to reduce the amount of noise read by the UV-Vis spectrophotometer from the LED. The irradiance values from the radiometer were corrected for the presence of the smaller cross-section area provided by the 3D printed cap. The reactions were conducted are several irradiance values.

A custom-made polycarbonate transparent box was built to enclose the CUV-ALL-UV 4-Way Cuvette Holder for oxygen-free experiments. The enclosure has fittings for every fiber optic cable described above, as well as gas fittings to allow the flow of nitrogen or argon during the experiments. The enclosure was sealed after assembled and before every experiment to ensure a positive pressure is built inside of the reaction chamber.

Initial experiments were performed in water without hydrogel precursor, e.g. polyethylene glycol diacrylate (PEGDA). However, coupled UV-Vis/FT-NIR allowed us to replicate these experiments with PEGDA to validate the proposed mechanism in polymerizing media, focusing on the $O_2$ inhibition.

Detection of Leuco Eosin Y and Fluctuations in Eosin Y Absorbance

A Cary 50 Bio UV-Vis Spectrophotometer (Varian Inc.—Agilent Technologies, Santa Clara, Calif.) was used to study the photoreduction of Eosin Y in the presence of TEOA and NVP. A custom-made green LED (530 nm) source was utilized to irradiate 3 ml aqueous solutions inside glass cuvettes. Discrete absorbance scans (<1 min) were taken at 20, 30 and 60 s intervals. The absorbance was also monitored after >95% of the Eosin Y was consumed. The irradiance of the green LED was estimated to be ~35 mW/cm$^2$ using an Advanced Light Meter (SPER Scientific, Scottsdale, Ariz.).

Light-Induced Hydrogel Formation

Plastic cuvettes with a 5 mm pathlength were filled with 1 ml aliquots of a solution containing 420 mM PEGDA, 35 mM NVP, 210 mM TEOA, and 5 μM Eosin Y in DI water. These solutions were irradiated with the same in-house built green LED (530 nm) source used for the photochemical detection of the leuco dye. First, samples were exposed for 10, 15, 20, 30, 40, and 60 s to the green LED alone. Then, samples were "sandwiched" between the green LED and the violet LED (405 nm) from an AmpliPHOX reader device (InDevR, Boulder, Colo.) with an irradiance of ~20 mW/cm$^2$. The start of irradiation was synchronized so that samples were exposed to 10, 15, 20, 30, 40 and 60 s of both the violet and the green LED's simultaneously. At the concentration and pathlength used, the thin film approximation was ensured. The spatial gradient of both light beams is expected to be negligible. After irradiation, the samples were stored in the dark. The extent of polymerization was determined qualitatively by comparing the extent of the gel formation inside the cuvettes. Samples irradiated with the green LED alone began gelling at around 20 s, while samples irradiated with both the violet and green LED's started gelling around 10 s of irradiation.

Theoretical Calculations of Physico-Chemical Properties

Marvin was used for drawing, displaying and characterizing chemical structures, substructures and reactions, Marvin version 16.8.1.0, release year 2016, ChemAxon.

Other embodiments are within the scope of the following claims.

What is claimed is:

1. A method of regenerating a photocatalyst comprising:
   irradiating the photocatalyst with a first range of wavelengths of light that excite the photocatalyst;
   forming visible-light absorbing metastable intermediates that increase efficiency, turnover number and turnover frequency of the catalyst and allow the photocatalyst to be regenerated by oxygen;
   enabling radical polymerization in the presence of oxygen;
   reducing or oxidizing the one or more intermediates; and
   simultaneously irradiating the one or more reduced or oxidized intermediates with a second range of wavelengths of light and oxidizing or reducing an excited state to turn the intermediate to the photocatalyst,
   wherein the first range of wavelengths of light and the second range of wavelengths of light are different
   thereby selectively accelerating photocatalyst regeneration, such that after oxygen depletion, the photocatalyst remains available for initiation.

2. The method of claim 1, wherein the one or more intermediates turns to the photocatalyst in the presence of oxygen.

3. The method of claim 1, wherein the photocatalyst is in a medium.

4. The method of claim 3, wherein the medium is aqueous.

5. The method of claim 3, wherein the medium is non-aqueous.

6. The method of claim 1, wherein the photocatalyst is Eosin Y.

7. The method of claim 6, wherein the first range of wavelengths of light is from 430 nm to 560 nm.

8. The method of claim 6, wherein the first range of wavelengths of light is from 516 nm to 525 nm.

9. The method of claim 6, wherein the second range of wavelengths of light is from 350 nm to 420 nm.

10. The method of claim 6, wherein the second range of wavelengths of light is from 405 nm to 408 nm.

11. The method of claim 1, wherein a concentration of a photocatalyst in the medium is 0.1-40 µM.

12. The method of claim 1, wherein an intensity of the first range of wavelengths of light is 0.75-35 mW/cm$^2$.

13. The method of claim 1, wherein the photocatalyst polymerizes hydrogel.

14. The method of claim 1, wherein the method is performed in a biphasic medium.

\* \* \* \* \*